United States Patent
Wechsler et al.

[11] Patent Number: 6,151,111
[45] Date of Patent: Nov. 21, 2000

[54] PHOTOMETRIC DEVICE

[75] Inventors: Mark Wechsler, San Mateo, Calif.;
Howard H. Barney, Portland, Oreg.;
Roger A. Kaye, Mountain View, Calif.;
David G. Ogle, Los Altos, Calif.;
Michael M. Lacy, Ben Lomond, Calif.;
Calvin Y. Chow, Portola Valley, Calif.;
Kimberly L. Crawford, Cupertino,
Calif.; Dean G. Hafeman,
Hillsborough, Calif.

[73] Assignee: Molecular Devices Corporation,
Sunnyvale, Calif.

[21] Appl. No.: 08/929,552

[22] Filed: Sep. 15, 1997

Related U.S. Application Data

[63] Continuation of application No. 08/606,080, Feb. 23, 1996, abandoned, which is a continuation of application No. 08/228,436, Apr. 15, 1994, Pat. No. 5,557,398.

[51] Int. Cl.$^7$ ..................................................... G01J 3/30
[52] U.S. Cl. .............................................................. 356/318
[58] Field of Search ..................................... 356/318–319,
356/325, 410, 328, 440, 436, 246, 427,
417; 250/227.23

[56] References Cited

U.S. PATENT DOCUMENTS

| | | |
|---|---|---|
| 4,545,680 | 10/1985 | Smith, Jr. . |
| 4,591,550 | 5/1986 | Hafeman et al. . |
| 4,652,127 | 3/1987 | Ekholm et al. .......................... 356/246 |
| 4,820,045 | 4/1989 | Boisde et al. . |
| 4,968,148 | 11/1990 | Chow et al. . |
| 5,002,392 | 3/1991 | Swope et al. ............................ 356/328 |
| 5,112,134 | 5/1992 | Chow et al. ......................... 356/436 X |
| 5,304,492 | 4/1994 | Klinkhammer . |
| 5,307,144 | 4/1994 | Hiroshi et al. ...................... 356/246 X |

FOREIGN PATENT DOCUMENTS 6039533   3/1985   Japan .

*Primary Examiner*—K. P. Hantis
*Attorney, Agent, or Firm*—McDonnell Boehnen Hulbert & Berghoff

[57] ABSTRACT

The present invention relates to a photometric device for measuring optical parameters. The invention functions in the ultraviolet light range through use of a monochromator and splits the test light in multiple channels by a rotor assembly, including a mirror.

15 Claims, 17 Drawing Sheets

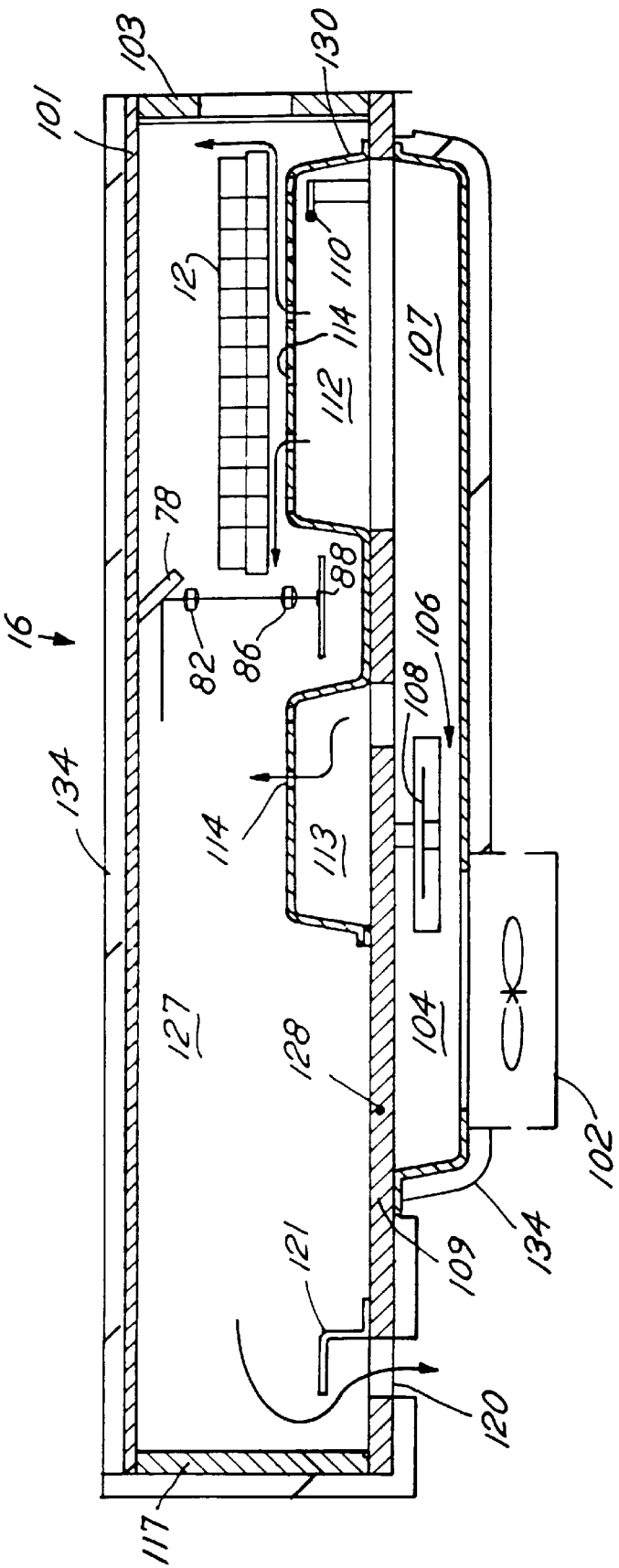

PHOTOMETRIC DEVICE

This application is a continuation of application Ser. No. 08/606,080, filed Feb. 23, 1996, now abandoned; which is a continuation of application Ser. No. 08/228,436, filed Apr. 15, 1994, now U.S. Pat. No. 5,557,398.

FIELD OF THE INVENTION

The present invention relates generally to photometric devices, such as those used to analyze blood, and more particularly to photometric devices utilizing ultraviolet light and a multi-assay plate having ninety-six (96) vessels arranged as eight (8) rows by twelve (12) columns, typically referred to as a microplate. U.S. Pat. Nos. 4,591,550; 4,968,148; and 5,112,134 concern photometric devices, and the teachings thereof are expressly incorporated herein by reference.

BACKGROUND OF THE INVENTION

A variety of techniques and devices are commercially available for the detection and measurement of substances present in fluid or other translucent samples by determining the light transmissivity of the sample. These can be broadly categorized into devices which measure the optical properties of one sample or a small number of samples essentially simultaneously and those which measure a large number of samples essentially simultaneously.

Photometric devices that simultaneously perform individual assays on a plurality of liquid or other translucent samples use a multi-assay plate which contains an array of vessels, such as eight rows by twelve columns (8×12), four rows by six columns (4×6), two rows by three columns (2×3), five rows by eight columns (5×8). Typically, the vessels of the multi-assay plate are spaced at nine (9) millimeter centers, have a volume of approximately four hundred (400) milliliters, and have a height of approximately one (1) centimeter. The multi-assay plate is made of material, such as polystyrene or polyethylene, that is optically transparent at the wavelengths of interest.

The optical density of the samples is measured by determining the amount of light attenuation. Light passing through the translucent samples, contained in the multi-assay plate vessels, is compared to a reference by conventional photodetectors.

A widespread use of multi-assay plates is in the enzyme-linked immunosorbent assay (ELISA) technique which is used for detection and quantitation of an extensive range of substances and biological cells in academic research and biotechnology as well as for clinical testing. In such assays, molecules of a marker enzyme (such as alkaline phosphatase) are deposited on the bottom and part way up the sides of each of the vessels of a multi-assay plate; each vessel having been assigned to interact previously, directly or indirectly, with a sample containing an analyte of interest. The number of marker enzyme molecules bound to each vessel of the plate is a function of the concentration of analyte in the sample of interest. Determination of the activity of the bound enzyme, therefore, permits detection or quantitation of the analyte.

For determination of fluid-phase enzyme activity, current techniques for both research and clinical applications employ kinetic analysis which involves measurement of the initial rate of enzyme-catalyzed, chromogenic reactions in the presence of excess of the enzyme substrate; a procedure which has several well known advantages over the alternative "end-point" analysis method of allowing the enzyme to react with a chromogenic substrate for a fixed period of time and then making a single optical density measurement after quenching the enzymes. In kinetic analysis, multiple readings are made within the interval (typically linear) reaction period and the intervals between readings are necessarily short (typically less than 30 seconds). By using kinetic analysis, the introduction of errors caused by (a) differences in initial optical density and/or (b) loss of independence from substrate concentration, is substantially avoided. Examples include the use of NADH and NADPH, as described, for example, in Lehninger, "Biochemistry, the Molecular Basis of Cell Structure and Function," Worth Publishers Inc., New York, 1970, and the teachings thereof are expressly incorporated herein by reference. Photometers capable of measuring the absorbance of ultraviolet light by NADH or NADPH at about 340 nanometers wavelength are particularly useful in performing such assays.

Currently available automated optical density measurement instruments for multi-assay plates regulate the temperature of the plate with radiant heating, i.e., heating a metal surface and radiating this heat onto the multi-assay plate. Alternatively, the multi-assay plates are heated by air convection, i.e., heating air and forcing it past the plate. A limitation of the existing air convection heating technology is that the plate takes a long time to warm up and reach equilibrium, adding to the time required to take measurements. Another limitation of existing technology is that the outer vessels, having more exposed surface area, warm up more quickly than the inner vessels and reach a different equilibrium temperature. The reaction rate and the rate of change of optical absorption for some specimens depend upon the temperature of the specimen. In a kinetic test of such specimens, a temperature difference between vessels leads to an erroneous result. Another limitation of existing technology is that moisture can condense on the optical components causing loss of focus and attenuation due to scattering of the light signal. Solvents contained in the moisture can cause corrosion on the surfaces of the optical, mechanical, and electrical components leading to further attenuation of the light signal and eventually to failure of the instrument.

Existing photometric devices capable of measuring multi-assay plates have been limited in the range and selectivity of the light spectrum that is provided for measurement and analysis. This limitation arises because the light source needs to be distributed to a plurality of samples, typically requiring multiple distribution elements and a vertical illumination of the samples. Proteins and Deoxyribonucleic Acids (DNAs) as well as many chromogenic substrates absorb at wavelengths shorter than 340 nanometers. Currently available photometric instruments that can operate at wavelengths less than approximately 340 nanometers are limited to assays on one or a small numbers of samples, thereby making large scale kinetic analysis assay applications impractical due to the extended sampling times. Additionally, currently available photometric instruments are limited to analysis at a single or small number of excitation wavelengths, thereby making overall full spectrum analysis impractical.

Another limitation associated with conventional photometric devices, when used for assaying chromogenic reactions kinetically, is that the conventional devices are subject to errors arising from erratic redistribution of the colored product as a result of phase separation and/or uncontrolled bulk movement of the aqueous phase of the sample during kinetic analysis. More specifically, in the case of ELISA protocols, where the enzyme is bound to the plastic surface of the multi-assay plate vessels (on the bottom and part way up the sides), the bound enzyme interacts with an unstirred aqueous phase layer which causes localized phase separation of the colored product of the enzyme reaction due to its high local concentration. This separation introduces an unquantifiable error and a degree of non-linearity into such kinetic measurements. Even in cases where the colored product remains in true solution, erratic bulk movement of the aqueous phase leads to uneven redistribution of the concentrated product and hence to an unquantifiable error.

Conventional multi-assay plate photometric measuring instruments are further limited in their utility by their use of interference filters in selecting a precise wavelength of test light. Fixed interference filters are constructed to provide a single predetermined test wavelength that cannot be easily changed. The user must change filters to change test wavelengths. Even with a filter wheel, measurements at more than a few wavelengths and spectrum measurements are impractical. Continuously variable interference filters are difficult to manufacture in a precisely reproducible way and photometric instruments with such filters are difficult to calibrate. Below 340 nanometers variable filters are difficult to manufacture so as to have adequate ultraviolet light transmission.

SUMMARY OF THE PRESENT INVENTION

In a first principal aspect, the present invention is a photometric device for measuring the optical properties of samples in multi-assay plates. An excitation light source and a monochromator provide essentially monochromatic test light which is distributed sequentially through a distribution network of optical fibers to illuminate and test the samples. A plate carrier moves the multi-assay plate so that each column of vessels is positioned, in turn, at a measurement station for illumination and testing. Photodetectors convert the test light passed by the samples into representative electrical output signals.

In a second principal aspect, the present invention relates to an improved test light generating system for use in a photometric device. The generating system includes a flash lamp to provide a series of light flashes having a first wavelength range. A monochromator responsively produces essentially monochromatic test light having a second wavelength range within the first. The system is capable of generating ultraviolet test light having a wavelength as low as 200 nanometers and as high as 1100 nanometers.

In a third principal aspect, the present invention relates to a beam splitter for splitting a reference from the test light. This split reference substantially avoids inaccuracies due to the inherent amplitude fluctuations in test light emitted by a flash lamp.

In a fourth principal aspect, the present invention relates to a mechanism for altering the direction of wavelengths of ultraviolet light as low as 250 nanometers without substantial loss of intensity. As is known in the art, "plastic" or "bendable" optical fibers absorb ultraviolet light and thus are unacceptable for applications requiring such light. Glass fibers, on the other hand, are not sufficiently flexible for use in nonlinear path applications, particularly where the radius of curvature is less than ten (10) times the fiber diameter.

The direction altering mechanism receives light emitted by an optical fiber in a first direction. The mechanism includes a rotor assembly having at least one mirror operable in a series of mirror positions. Each position corresponds to an altered light transmission direction. The rotor assembly accommodates a nonlinear light path, including both folded and curvilinear paths, as is typically is required by the geometry of the device. The rotor assembly significantly reduces the number of components otherwise required by changing "single channel" light from a source into "multiple channel" light for transmission to multiple vessels of the multi-assay plate.

In a fifth principal aspect, related to the fourth aspect, the present invention relates to a photodetector device utilizing a flash lamp, wherein "single channel" light is split to provide a reference prior to conversion into "multiple channel" light. The reference light is used to detect the inherent amplitude variations in the light emitted from such an excitation light source.

In a sixth principal aspect, the present invention relates to a temperature control mechanism for use in conjunction with a photometric device for measuring optical properties of samples within vessels of a multi-assay plate. The control mechanism regulates the temperature of the samples during the optical measurement process and provides substantially uniform and rapid heating of the samples disposed in the multi-assay plate. The temperature control mechanism includes a housing, substantially enclosing the multi-assay plate in a closed state, and a supply of heated air. The heated air flows through apertures in a baffle, impinging upon the exposed surfaces of the multi-assay plate. The apertures are arranged or sized so that the central vessels in the multi-assay plate receive a greater flow of heated air than the peripheral vessels so as to achieve a substantially uniform heating rate and final temperature.

In an seventh principal aspect, the present invention relates to a microprocessor-based photometric device. The processor controls the operation of the device, including measurement of the electrical signals representative of the light that has passed through the samples and temperature control of the chamber surrounding the multi-assay plate. Preferably the processor includes a key entry system and a display, such that tests can be initiated and sequenced and test results can be displayed and printed. The typical test results represent light absorbance, light scattering, fluorescence and/or phosphorescence.

It is thus an object of the present invention to provide an economical, readily maintainable photometric device. It is also an object to provide a photometric device operable in the ultraviolet range, i.e., at a wavelength as low as 250 nanometers. Another object is a multi-assay plate photometric device having simplicity in terms of structure and operation. Still another object is a photometric device capable of accurate measurement at a speed of less than ten (10) seconds per microplate.

Another object is to provide a photometric system wherein light initially is carried from the source by a single optical fiber, substantially reducing necessary parts and components and substantially facilitating wavelength adjustment and amplitude sampling of the light. Still another object of the present invention is an improved mechanism for redirecting light from a single optical fiber to a series of distribution optical fibers corresponding to the vessels in each column of a multi-assay plate. Yet another object is a light redirecting mechanism utilizing a rotatable mirror to substantially avoid loss in the amplitude of the redirected light.

It is a further object of the present invention to provide a photometric device, utilizing a multi-assay plate, wherein fluid sample temperature is highly regulated. Another object is a temperature control system substantially reducing the accumulation of flammable vapor from the fluid samples (such as hexane, isooctane, and nitromethane) within the housing, thereby substantially decreasing the potential hazard of a fire or an explosion. Yet another object of the invention is to substantially avoid condensation within the housing of the photometric device.

These and other features, objects and advantages of the present invention are set forth or implicit in the following detailed description.

BRIEF DESCRIPTION OF THE DRAWING

Preferred embodiments of the present invention are described, in detail, with reference to the drawing wherein:

FIG. 3a is a cross-sectional view of the photometric device in a closed state;

FIG. 3b is a partial cross-sectional, partial top view of the embodiment shown in FIG. 3a;

DETAILED DESCRIPTION OF PREFERRED EMBODIMENTS

Figure 1:
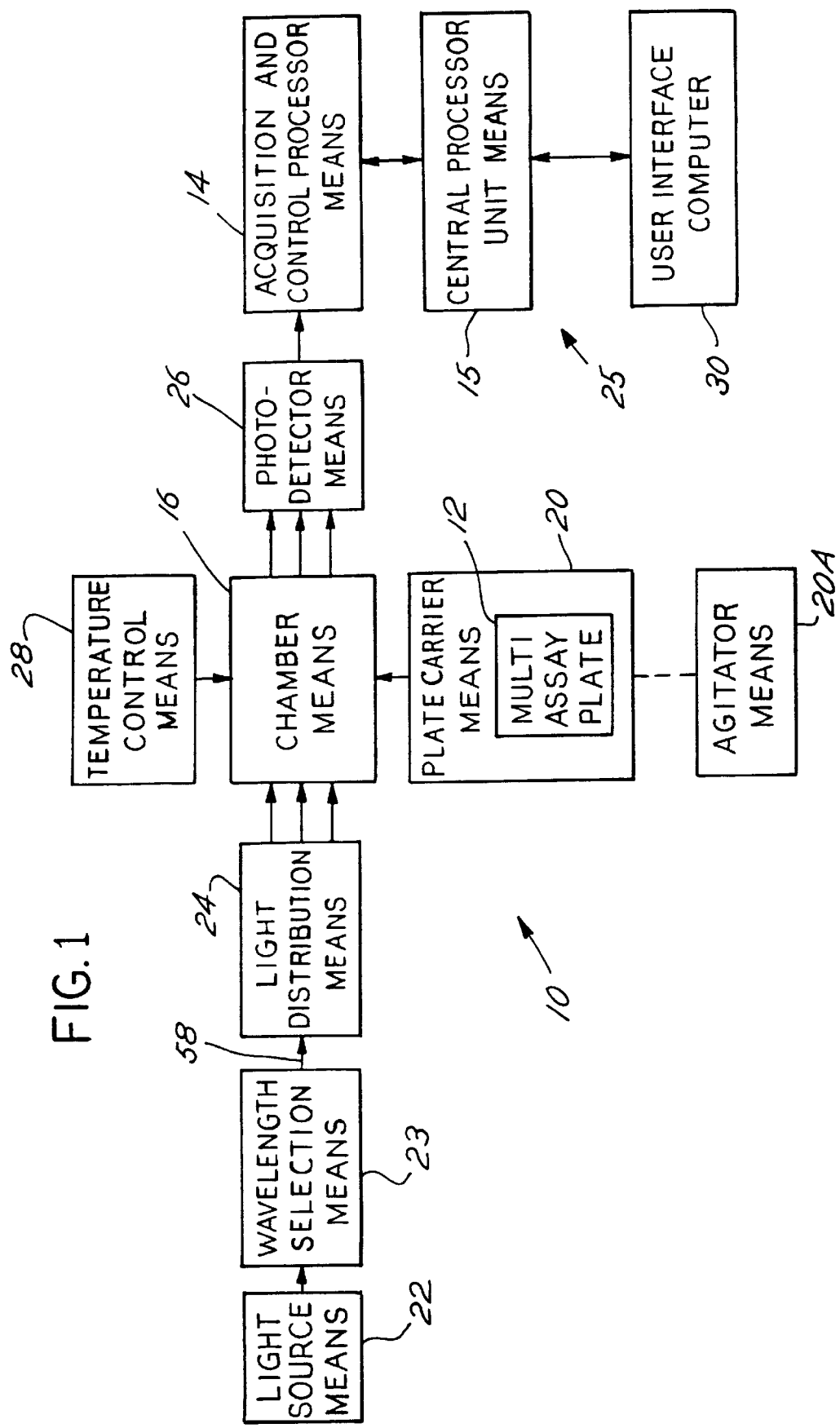
FIG. 1 is a block diagram illustrating the major components of the photometric device.

Referring to FIG. 1, a preferred embodiment of the present invention is shown as a photometric device or measurement system, generally designated 10, for testing fluid samples contained in vessels in a multi-assay plate 12. The multi-assay plate 12 is a conventional microplate, including a standard array of vessels arranged in eight (8) rows by twelve (12) columns (8×12). The photometric measurement system 10 includes and operates, in a conventional manner, under the direction and control of an acquisition and control processor means 14, a central processing unit means 15, and a user interface computer 30, as further described herein, which cooperatively define processor means 25 for initialization, set-up, data acquisition, analysis and display.

A light source means 22 emits a band of wavelengths of light having a first wavelength range of approximately 200 nanometers to approximately 1100 nanometers. A desired, essentially monochromatic light, with a wavelength in the range of 250 to 750 nanometers, is selected by a wavelength selection means 23 and delivered through an optical fiber 58 to a light distribution means 24. The light distribution means 24 delivers eight (8) channels of test light (representatively shown in FIG. 1) sequentially to the samples in a column of eight (8) vessels of the multi-assay plate 12 and delivers one channel of reference light, used to substantially eliminate errors in measurement due to the variations over time in light amplitude emitted from the light source means 22. A photodetector means 26 detects and measures both the test light that has passed through the vessels and the reference light. The acquisition and control processor means 14, coupled to the photodetector means 26, provides electrical output signals in a conventional manner, in accordance with the reference light and the test lights.

The photometric measurement system 10 includes a chamber means 16, having an open and closed state and an entry/exit door 111, for housing the multi-assay plate 12. A plate carrier means 20 receives, peripherally supports and carries the multi-assay plate 12 from a loading position remote from the chamber means 16 to a measurement station therein, sequentially advancing each column of vessels to the measurement station. The chamber means 16 and plate carrier means 20 operate in a conventional manner.

A temperature control means 28, under control of the acquisition and control processor means 14, maintains the temperatures of the fluid samples in the multi-assay plate 12 at a uniform level preselected by a user. The temperature control means 28 directs a heated air stream in a predetermined pattern to the underside of the multi-assay plate 12, and thereby provides substantially uniform and rapid heating of the samples to the predetermined temperature.

The central processing unit means 15 initializes the acquisition and control processor means 14, and the user communicates with the unit means 15 through the user interface computer 30. The user interface computer 30 contains application programs which set measurement parameters, perform analysis and display results for the user.

Figure 2:
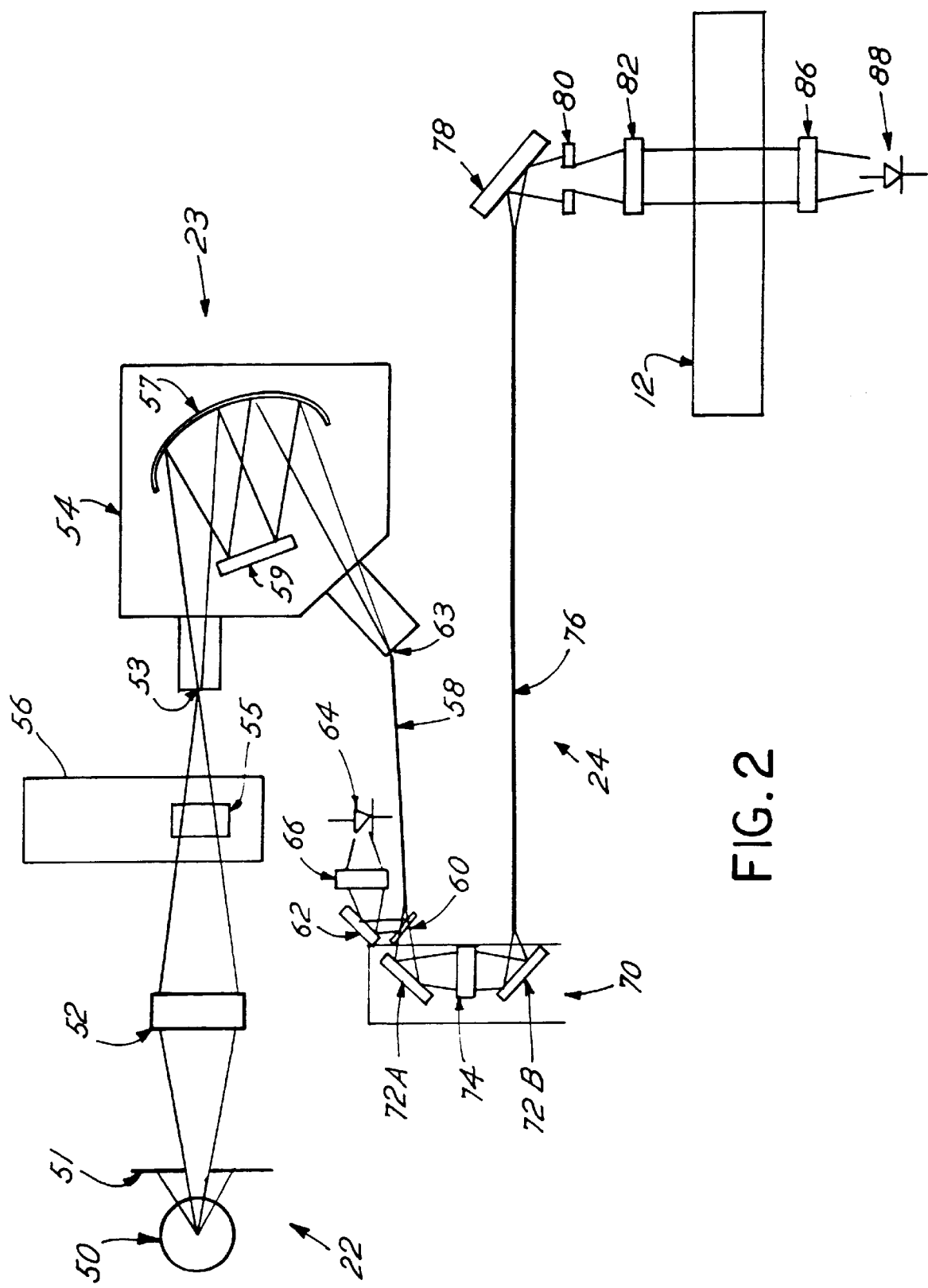
FIG. 2 is a schematic of the optical system of the preferred embodiment of the present invention shown in FIG. 1.

With reference to FIG. 2, the photometric device 10 produces a beam of essentially monochromatic light in the form of flashes and delivers this light sequentially to a plurality of light channels, eight in this preferred embodiment, to sequentially illuminate the fluid samples in the multi-assay plate 12.

An excitation light source 50, a Xenon flash lamp in this preferred embodiment, emits light flashes containing wavelengths between at least 200 nanometers and 1100 nanometers. Light from the excitation light source 50 beams through an aperture 51 limiting the light arc to approximately ten degrees (10°). This light then passes through a source lens 52, which focuses the light through one of a series of filters 55, included in a filter wheel 56, upon a monochromator, generally designated 54. The excitation light source 50, aperture 51, and source lens 52 cooperate to define the light source means 22.

The source lens 52, in this preferred embodiment, is a fused silica plano-convex lens with a 12.7 millimeter diameter, a 16 millimeter focal length, and an optical magnification of 1. The source lens 52 is spaced 32 millimeters from the excitation light source 50 and 32 millimeters from the monochromator 54.

Figure 16:
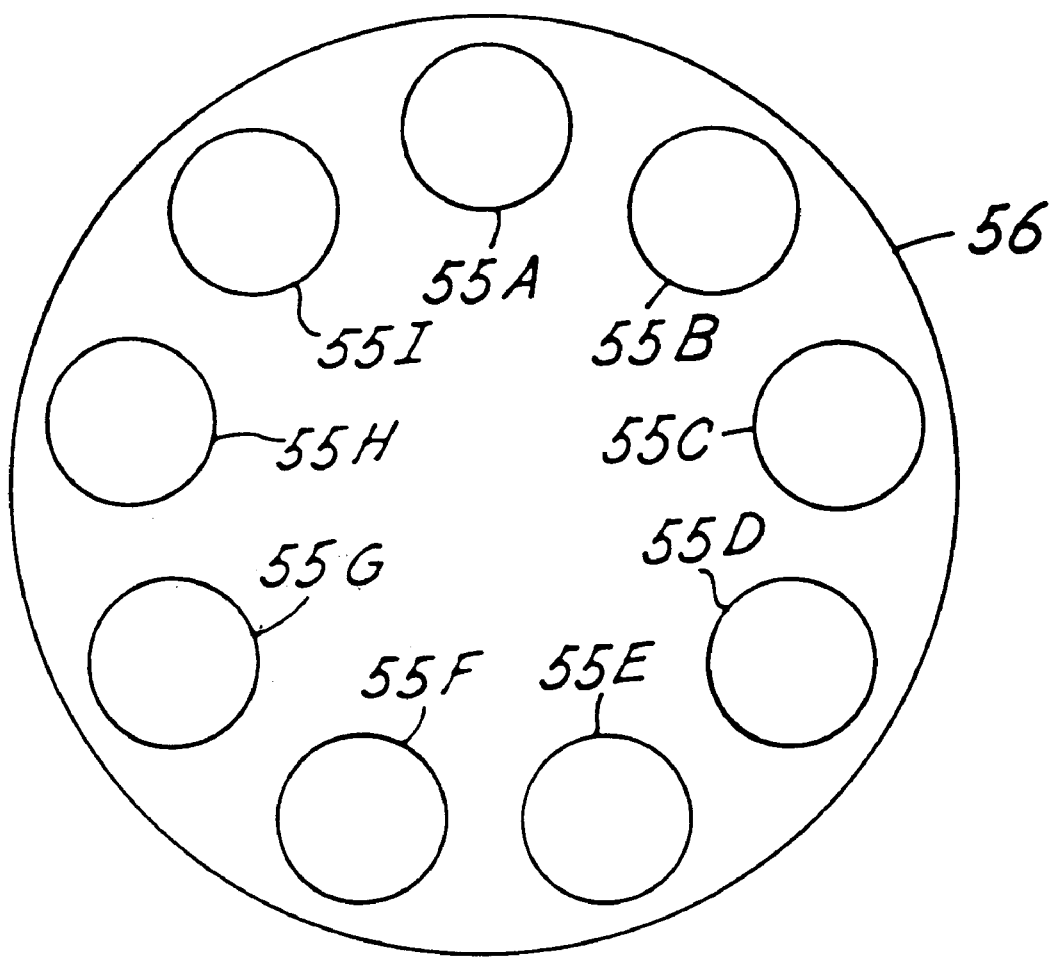
FIG. 16 is a front view of the filter wheel incorporated into the optics system of the photometric device shown in FIG. 1.

With reference to FIG. 16, there are seven (7) filters 55A–G on the filter wheel 56. The filters 55A–E pass light of wavelengths in the range of 250 to 380 nanometers (commonly referred to as a UG 5 filter), 380 to 440 (BG 37), 440 to 530 (VG 6), 530 to 630 (OG 550) and 630 to 750 (RG 645). The remaining filters are a Didymium glass filter 55F, used in the initial calibration of the monochromator 54, and a dark filter 55G, also used for calibration. The multiple glass filters 55 preselect ranges of wavelengths received by the monochromator 54 to substantially eliminate broadband light signals, especially sub-harmonics of the desired wavelength that otherwise would be passed by the monochromator 54 to contaminate the light spectrum. This preselection enables the monochromator 54 to emit wavelengths of substantially monochromatic light with a bandwidth of approximately 5 nanometers over a range of wavelengths of greater than two to one, or from 250 nanometers to 750 nanometers. The Didymium glass filter 55F provides a precise, narrow absorption wavelength used in the initial wavelength calibration of the monochromator 54. A low-pressure Mercury-Argon lamp verifies the spectrum of the Didymium glass as a part of the manufacturing process before the installation of the Didymium glass filter 55F into the photometric device 10. Two additional open filter positions 55H and I are provided where the user can install filters for custom usage. For example, the user may install interference filters in order to select a light band that is less than approximately 5 nanometers. The dark position 55G of the filter wheel 56 is used to ensure that no light illuminates the reference photodetector 64 during the measurement of reference dark current offset calibration.

Light enters the monochromator 54 through a monochromatic entrance slit 53 to a collimating/focusing mirror 57 which reflects and collimates the light beam to a diffraction grating 59. There the light is dispersed at an angle with respect to the grating 59 and the wavelength of light passed by the monochromator 54 is dependent upon this angle. The dispersed light falls back on the collimating/focusing mirror 57 which focuses substantially monochromatic light to an exit slit 63. This slit 63, preferably formed by a metal end cap (not shown) which retains the fibers 58A of the optical fiber 58, is rectangular in shape, 0.7 millimeters by 1.3 millimeters. The individual optic fibers are arranged in a rectangular array at the exit slit 63 by the metal end cap. Alternatively, the outer cladding of the optical fiber 58 may be formed into the exit slit 63. The filter wheel 56, optical filters 55, monochromator 54 and entrance and exit slits 53, 63 cooperate to define the wavelength selection means 23.

The output of monochromator 54 provides light having a predetermined, continuously selectable, second wavelength range within the first wavelength range provided by light source 50. In the preferred embodiment disclosed herein, the second wavelength range has a predetermined bandpass width, defined as the wavelength width at one-half maximum light transmission, of about 4 to 5 nanometers for all center-band wavelengths continuously selectable by the user between 250 and 750 nanometers. The bandpass width may be predetermined within a wider range of about 1 to 20 nanometers by changing the width of the exit slit 63, e.g., by employing a mechanically adjustable slit as the exit slit 63.

The optical fiber 58 includes nineteen (19) optical fibers, each 200 millimeters in diameter with a numerical aperture of 0.22 arranged at the input in three (3) rows of six (6), seven (7), and six (6) fibers. This effectively defines a 0.7 millimeter by 1.3 millimeter rectangular exit slit 63. The output of the optical fiber 58 is configured as a circle with a diameter of 1.3 millimeters. Light from output of the optical fiber 58, which is emitted over a solid angle of about ten degrees, is split by a beam splitter 60, a sapphire window in this preferred embodiment. The beam splitter 60 splits the light into a test light that passes through the beam splitter 60 to a rotor assembly 70 and a reference light that reflects from the beam splitter 60 to a flat reference mirror 62. The reference mirror 62 reflects the reference light through a reference lens 66 to a reference photodetector 64 of the photodetector means 26. The reference lens 66 is a bi-convex lens, is made of fused silica, has a focal length of 6.8 millimeters, and has a diameter of 6.8 millimeters.

The intensity of light flashes emitted by the Xenon flash light 50 may vary as such a 50% between successive flashes due to variations in the energy and path length. The reference photodetector 64 outputs an electrical signal representative of the amplitude of the monochromatic light carried by the optical fiber 58 for each flash of the light excitation source 50. This electrical signal is used as an intensity reference for the readings of test light transmitted through samples in the multi-assay plate 12.

The rotor 70 includes two substantially identical rotor mirrors 72A and 72B to bend the light by 180 degrees and a rotor lens 74 to focus the light beam between the rotor mirrors 72A and 72B. The rotor mirrors 72a and 72B and the rotor lens 74 act to reduce the spot size of the light beam from 1.3 millimeter diameter at the input of the rotor 70 assembly to 0.65 millimeters at the output. The reduction in beam diameter within the rotor 70 allows substantially all of the light to be launched at a solid angle of about 20 degrees into the receiving fibers 76 of the light distribution means 24, greatly enhancing efficiency of test light transmitted through the rotor 70. Care is taken so that the test light is not focused in such a way that it exceeds the numerical aperture of the distribution optical fibers 76 which will accept light over a solid angle of about 24 degrees.

Most existing methods of redirecting light into multiple curvilinear channels use bent or curved fibers to accomplish the bend of the light beam. Plastic materials bend readily into the required curvatures but below approximately 340 nanometers most plastics are highly absorptive. Materials that transmit wavelengths of less than approximately 340 nanometers are difficult to bend. Further, systems which rely upon optical fibers to bend light cannot by their nature reduce the size of the image to increase efficiency. A primary feature of the rotor 70 as described is that it uses air as the transmission medium. An air medium enables the system to redirect the light without the high absorption loss of plastic materials and to increase efficiency of light transmission by reducing the size of the output beam.

The rotor assembly 70 distributes the test light to a dark channel, to calibrate for offset, or to one of a series of optical distribution channels, as determined by the sequence in the measurement. The optical distribution channels are defined by the distribution optical fibers 76, made of solid silica or quartz, 1 millimeter in diameter, with a numerical aperture of 0.22. Light from the fibers 76 reflects off a test mirror 78, made of $MgF_2$ with a flat surface, into a substantially vertical test light direction. A test aperture 80 further limits the numerical aperture of the beam, and a test lens 82 and test photodetector lens 86, each a bi-convex lens, fused silica with 6.8 millimeter focal length and 6.8 millimeter diameter, further focus the test light. For ease of illustration, FIG. 2 shows only one of the eight substantially identical distribution optical fibers 76, test mirrors 78, test apertures 80, test lenses 82 and test photodetector lenses 86.

The series of optical distribution channels sequentially illuminate the multiplicity of samples in the multi-assay plate 12 with test light, such that each of a multiplicity of samples receives test light having a substantially identical spectral distribution of light intensities within the second wavelength range provided by the monochromator 54. The photometric device 10 described provides the above test light characteristics to a multiplicity of samples in a multi-assay plate within a short period of time so that the single measurement optical properties of 96 samples contained in a conventional 8×12 microplate may be determined in approximately 9 seconds. Similarly, optical properties of such 96 samples may be determined kinetically with about 9 seconds between repetitive optical measurements on each sample. Furthermore, such kinetic measurements of optical properties, selected from within a continuously variable wavelength range of 250 to 750 nanometers, may be made while samples within the multi-assay plate are agitated by repeated oscillatory movement with less than about 9 seconds between cessation of agitation and final measurement. As shown in FIG. 1, the photometric device 10 includes agitator means 20A of a conventional nature for intermittently vibrating the multi-assay plate 12 and mixing the samples. The optical fiber 58, beam splitter 60, reference mirror 62, reference lens 66, optical distribution channels 76, and the rotor 70, including rotor mirrors 72A and 72B, and rotor lens 74 cooperate to define the light distribution means 24.

After passing through the samples, the test light continues to the test photodetectors 88. The light distribution means 24 employs a multiplicity of individual optical fibers, arranged in a rectangular array at the exit slit 63 of monochromator 54, to pass test light vertically through a multiplicity of samples disposed on the multi-assay plate 12 to the photodetectors 88.

The multi-assay plate 12 is contained in an assay plate compartment 127 within the chamber means 16. Under control of the processor means 25, the multi-assay plate 12 is moved from the remote loading station into the compartment 127 and the door 111 is closed. Importantly, each of the multiplicity of samples receives test light having a substantially identical spectral distribution of light intensities provided within the second wavelength range of light provided by the monochromator 54. In this preferred embodiment, the statistical mean wavelength of light energy will vary by less than 0.1 nanometers in the distribution optical fibers 76. In no case, for wavelengths between 250 and 750 nanometers, will the statistical mean wavelength of light energy will vary by more than 0.5 nanometers in the distribution optical fibers 76. Where a sample within the multi-assay plate 12 contains a substance absorbing or otherwise affecting light transmission (e.g., light scattering or light refraction), at wavelengths between 250 and 750 nanometers, the substantially identical spectral distribution of light intensities delivered to each sample on the multi-assay plate 12 insures that a substantially uniform result of measured optical properties will be reported by the photometric device 10. The substantially identical spectral distribution of light intensities, from 250 to 750 nanometers wavelength, delivered to each sample on the multi-assay plate 12 is enabled by the deployment of the quartz optical fiber 58, as a bundle with rectangular shape, at the exit slit 63 of the monochromator 54. The light so collected is directed as test light, substantially unchanged in spectral distribution by the rotor assembly 70, to the optical distribution fibers 76.

Uniform spectral light distribution by splitting of the optical fiber 58 directly may be employed as an alternative embodiment of the present invention. In this case, each optical distribution channel 76 will be associated with a beam splitter 60, a reference mirror 62, reference lens 66, and a reference photodetector 64, along with the required photodetector circuitry. The simplest case involves eight (8). silica light distribution optical fibers of about 0.5 mm diameter, arranged in a linear fashion parallel to and centered within the exit slit 63. In general, however, the distribution of spectral light intensities delivered to each distribution optical fiber 76 will be substantially more uniform when the rotor 70 is employed.

Figure 4:
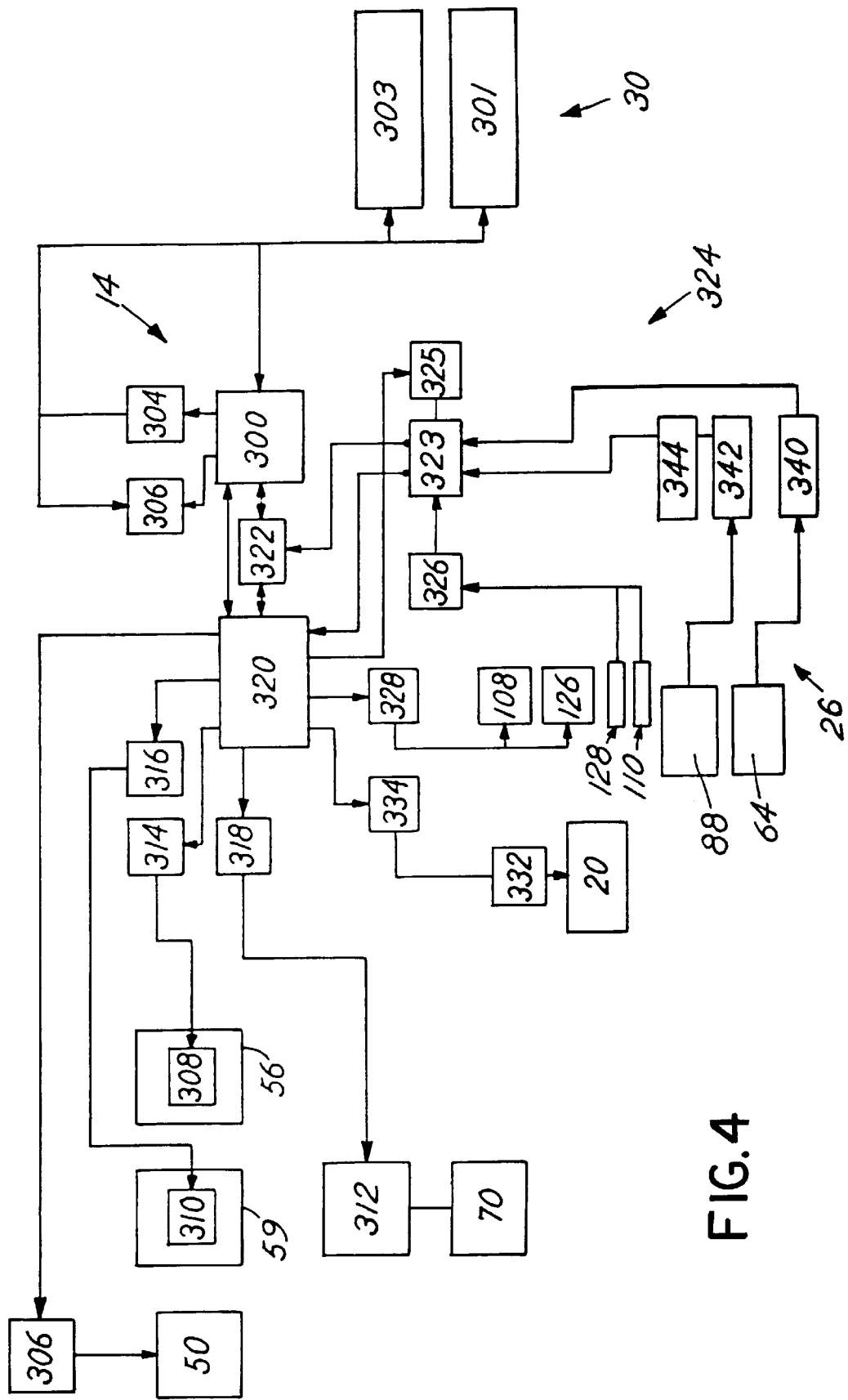
FIG. 4 is an electrical schematic diagram according to a preferred embodiment of the present invention.

Each of the optical distribution channels 76 corresponds to a series of electrical channels including a test photodetector 88. The reference photodetector 64 and the photodetector 88 are silicon photodiodes with 9.6 millimeter active area and 150 picofarads junction capacitance, to detect the test light and provide a representative electrical signal as an output to a test channel in an integrator 342 of the electrical measurement system 324, as shown in FIG. 4.

A conventional 96-well microplate or other multi-assay plate may be used to contain samples in this preferred embodiment of the photometric device 10. In order to measure light transmission at wavelengths of less than approximately 330 nanometers, however, a special multi-assay plate should be used in order to insure adequate transparency in this ultraviolet portion of the electromagnetic spectrum. Multi-assay plates made of quartz, sapphire or other UV-transparent materials may be used. Such quartz microplates are available from Molecular Devices Corporation of Menlo Park, Calif., e.g., Part Nos. R1077 and R1076. In addition, a polymeric multi-assay plate which is adequately transparent over the entire wavelength range of 250 to 750 nanometers is described in copending and commonly owned Ser. No. 08/228,415, now U.S. Pat. No. 5,487,872, filed concurrently herewith and entitled "Ultraviolet Radiation Transparent Multi-Assay Plate", and the teachings thereof are expressly incorporated herein by reference.

With reference now to FIG. 3a, the photometric device 10 includes an isothermal chamber 127 and a temperature control for maintaining the temperature of the samples in the multi-assay plate 12 at a predetermined level. A fan 102 drives ambient air through an enclosed plenum 104 into a narrow passageway 106 about an air-heating element 108, which heats the air to a predetermined temperature. The air heated by the air-heating element 108 moves into a post-heating passageway 107 and then through openings in an interior base wall 109 to a major post-heating plenum 112 and a minor post-heating plenum 113. An air temperature sensor 110 in the major post-heating plenum 112 measures the temperature of the heated air so that the air-heating element 108 may be controlled to provide the desired, predetermined air temperature.

Figure 3B:
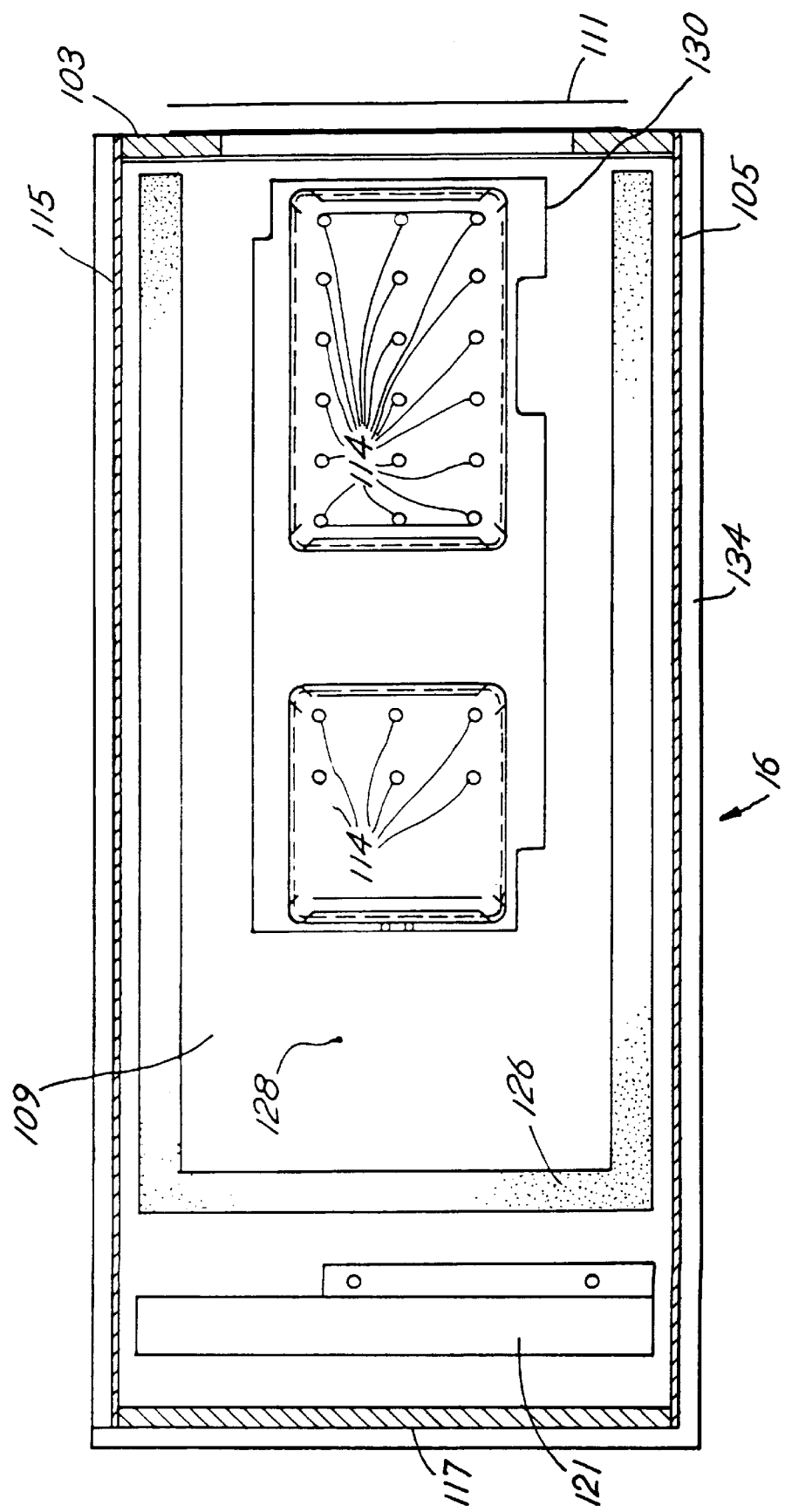

The heated air continues from the major post-heating plenum 112 and minor post-heating plenum 113 through apertures 114 in a baffle 130, as best shown in FIG. 3b. The apertures 114 direct heated air to predetermined regions of the multi-assay plate 12 disposed in a multi-assay plate compartment or chamber 127 located above the baffle 130. The multi-assay plate compartment 127 is enclosed by a top wall 101, door-side wall 103, door-opposed side wall 117, interior base wall 109, as well as by a front side wall 105, back side wall 115 and the closed door 111, as shown in FIG. 3b. The multi-assay plate compartment 127, in this preferred embodiment, is thermally isolated from ambient air by insulation 134, one quarter inch (¼") polyurethane foam about the chamber or compartment 127, except for the door-side wall 103 and door 111. The door-side wall 103 is insulated on the inner surface facing the compartment 127 with one-sixteenth inch (1/16") polyurethane. The door 111 is formed of Noryle® (as manufactured by General Electric Corp.) and is not insulated additionally.

The temperature of the fluid samples in the multi-assay plate 12 is maintained within a range of approximately plus or minus one half (½) degree Centigrade in a typical laboratory environment of approximately twenty-three (23) degrees Centigrade. Cooled air is guided by an air guide 121 out of the multi-assay plate compartment 127 through an exit port 120. The door 111 allows entry and exit of the multi-assay plate 12 from the multi-assay plate compartment 127 in a conventional manner.

Solvents, such as water, hydrochloric acid and nitric acid, in the fluid samples in the multi-assay plate 12 may evaporate from the fluid samples and be absorbed by the heated air. To prevent condensation of these solvents within the photometric device 10, an interior wall heating element 126, as shown in FIG. 3b, together with a chamber wall temperature sensor 128 in the interior base wall 109, maintain the inside surface of the chamber 127, near the temperature sensor 128, at a predetermined housing temperature slightly (generally from 0.5 to 2.0° C. and more generally from 0.5 to 1.0° C.) greater than the temperature of the heated air. The fan 102, air-heating element 108, air temperature sensor 110, wall heating element 126, chamber wall temperature sensor 128, baffle 130, and the associated control circuitry described below with reference to FIG. 4, cooperate to define the temperature control means 28.

FIG. 3b illustrates one arrangement of the apertures 114 in the baffle 130. This arrangement of the apertures 114 directs an increased flow of heated air to the center vessels of the multi-assay plate 12 (which have less surface area and consequently heat more slowly than the outer vessels of the multi-assay plate 12) so that all vessels of the multi-assay plate 12 will reach a predetermined temperature at an equal rate. The apertures 114 may be shaped and directed as nozzles to direct heated air in desired directions. Alternatively, the inside apertures, directed to the inside vessels, can have a larger diameter than the outside apertures, directed to the outside vessels, so the inside vessels receive more heated air than the outside vessels and so that all vessels will reach the equilibrium temperature at an equal rate.

FIG. 4 illustrates the electrical components of the photometric device 10, including a 68000-type microprocessor, memory and associated digital hardware. The user communicates with a central processor (CPU) 300 through a keypad 301, a display 303, a printer port 304, and a serial port 305. The CPU 300 initializes and controls the acquisition and control processor means 14 through a programmable logic device (PLD) 322, such as manufactured by Altera corporation of San Jose, Calif. The CPU 300, printer port 304, serial port 305 and PLD 322 cooperate to define the central processing unit means 15, and the keypad 301 and display 303 cooperate to define the user interface computer 30.

A control processor 320 controls the electrical measurement system 324. The electrical measurement system 324 includes a digital to analog converter (DAC) 325 used in the calibration of the photometric device 10, a series of test channels in an integrator 342, a reference integrator 340, a multiplexer 344, and an amplifier/ADC 323. A series of eight test photodetectors 88 and a reference photodetector 64 provide electrical signal pulses representative of test light and reference light flashes to the series of test channels of the integrator 342 and the reference integrator 340, respectively. The integrators 340, 342 integrate and provide as output signals the respective energies in the electrical pulses received from the test photodetectors 88 and reference photodetector 64, respectively. The PLD 322, in response to the control processor 320, times start and completion of the integration provided by the integrators 340, 342. The multiplexer 344 receives the integrated output signals from the integrators in parallel and multiplexes these signals to serial. The amplifier/ADC 323 amplifies and converts analog signals from the multiplexer 344 into digital signals. An electrical channel includes the reference photodetector 64 or the test photodetector 88 and the corresponding reference integrator 340 or integrator 342. The reference photodetector 64, test photodetectors 88, and electrical measurement system 324 cooperate to define the photodetector means 26.

A temperature sense circuit 326 receives and amplifies the output of the electrical signals from the air temperature sensor 110 and chamber wall temperature sensor 128, which represent the temperatures of the heated air in the narrow passageway 106 and the interior base wall 109, respectively. The amplified signals are provided as outputs to the amplifier/ADC 323. The amplifier/ADC 323 further amplifies and converts from analog to digital form the signals from the temperature sense circuit 326. Acquisition and control processor 320 receives these signals from the amplifier/ADC 323 representative of the wall and air temperatures and outputs signals through a heater driver 328 to wall heater 126 and air heater 108 to control the temperature of the fluid samples in the multi-assay plate 12 to a predetermined level.

The acquisition and control processor 320 operates in a conventional manner (i) to control the time of the flashes emitted by the excitation light source 50 through an excitation light source power supply 306, (ii) to control the position of the filter wheel 56 through a filter wheel driver circuit 314 and filter wheel stepper motor 308, (iii) to control the diffraction grating 59 in the monochromator 54 through a monochromator driver circuit 316 and a stepping grating motor 310, (iv) to control the rotor 70 through a rotor driver circuit 318 and a stepper rotor motor 312, and (v) to control the plate carrier means 20 through a plate carrier driver circuit 334 and an stepper plate carrier motor 332. The control processor 320, excitation light source power supply 306, filter wheel driver circuit 314, filter wheel stepper motor 308, monochromator driver circuit 316, stepping grating motor 310, rotor driver circuit 318, stepper rotor motor 312, plate carrier driver circuit 334, and stepper plate carrier motor 332 cooperate together to define the acquisition and control processor means 14.

Figure 5:
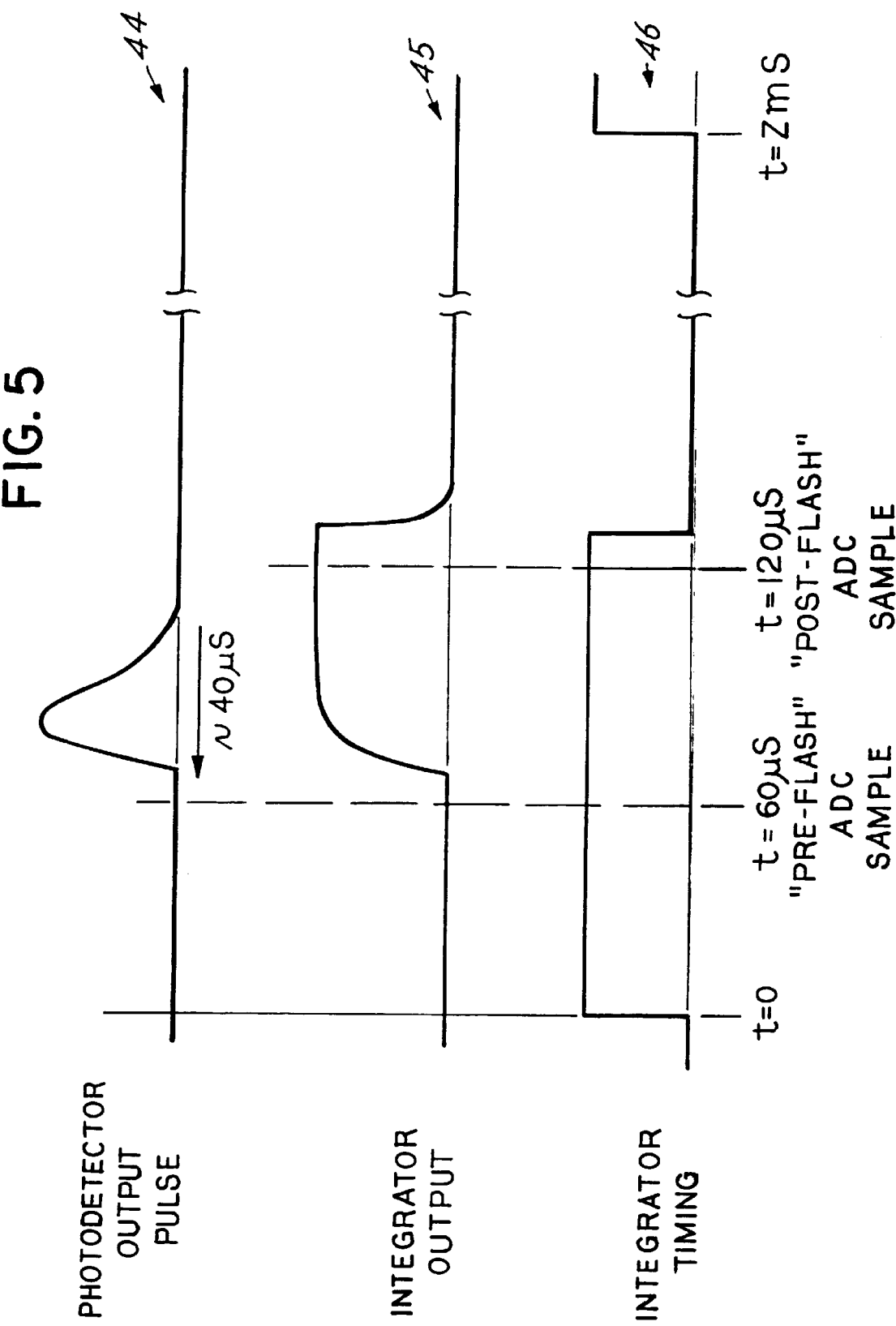
FIG. 5 is a timing diagram relating to the measurement processes performed by the present invention.

FIG. 5 illustrates the timing of the integrator 342 and reference integrator 340 in the electrical measurement system 324. Light flashes are emitted by the excitation light source 50 and delivered to the reference photodetector 64 and test photodetectors 88. In waveform 44, the reference photodetector 64 and test photodetector 88 provide electrical pulses representative of the light flashes. In waveform 45, the integrator 342 and the reference integrator 340 integrate and provide an output signal representing the total energy present in the electrical pulses provided by the photodetectors. In waveform 46, the integrator 342 and reference integrator 340 outputs are sampled at times determined from the PLD 322 before the electrical pulse at time "pre-flash" when the energy of the pulse is still approximately zero and again at "post-flash" when approximately all the energy in the electrical pulse has been integrated. The signals from the integrator 342 and reference integrator 340 are calibrated for offset in the integration process by subtracting the "pre-flash" reading from the "post-flash" reading. In waveform 46, a timing signal zeros the integrator 342 and the reference integrator 340 after the "post-flash" to prepare for the next pulse.

Some noise is always present to contaminate an electrical measurement and the precision and repeatability of the measurement are improved when the noise is minimized. A benefit of the technique described above, using a flash light, is that the amount of noise contaminating the measurement is accumulated only during the integration time, as compared to a technique using a continuous light source, when noise is accumulating at all times. The technique used in the preferred embodiment reduces the noise in the measurement approximately by the ratio of the integration time to the cycle time.

Figure 6:
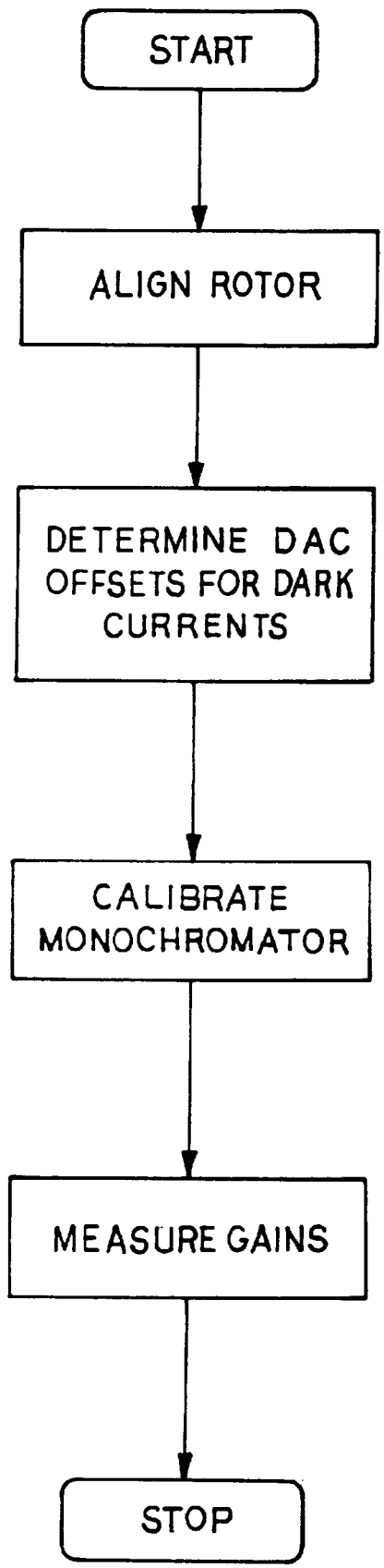
FIG. 6 is a flow chart of the power-up sequence for a preferred embodiment of the present invention.

FIGS. 6, 7, 8, 9, 10, 11, 12, and 13 below illustrate the sequence of operations involved in a sequential measurement of the optical properties of the samples in vessels in the multi-assay plate 12 according to the present invention. FIG. 6 is a flow chart illustrating the sequence undergone by the photometric device upon power-up. Step 140 uses an iterative process under control of the acquisition and control processor 320 to align the rotor 70 to maximize the light transmitted through the optical distribution channels.

In step 142 the coarse "dark current" offset calibrations are determined. Dark current is the apparent light that the electrical measurement system 324 reads from each of the photodetectors when no light is transmitted. A dark current offset calibration is determined for each in the series of test channels in the integrator 342 for each gain setting in the amplifier/ADC 323. Step 142 aligns the rotor 70 to a dark position where light does not pass to the series of optical distribution channels. The DAC 325, included as a part of the electrical measurement system 324, is adjusted to provide a differential input signal to each in the series of test channels in the integrator 342 where the input signal compensates for the effect of dark current. An iterative process under the control of the acquisition and control processor 320 is used to find and store DAC 325 adjustments that minimize the apparent light measurement in each of the series of optical distribution channels and corresponding test channels in the integrator 342 for each gain setting of the amplifier/ADC 323 and for the reference integrator 340. The DAC 325 adjustments so determined are used as coarse dark current offset calibrations in the sequence described in greater detail in FIG. 9 below.

At step 144 the-wavelength of the light selected within the monochromator 54 is calibrated. A Didymium glass filter having a known wavelength absorption spectrum, included in the filter wheel 56, is used as a wavelength calibrator within the photometric device. To calibrate the wavelength of the monochromator 54, step 144 turns the filter wheel 56 to the position where the light received by the monochromator 54 passes through the Didymium glass filter. The angle of the monochromator 54 in relation to the light beam it receives is then adjusted by stepping the grating motor 310 under control of the control processor 320 to minimize the light detected by the reference photodetector 64. The adjustment of the grating motor 310 stored in memory is the wavelength offset calibration of the monochromator 54.

Step 146 calibrates the gain of the amplifier/ADC 323. The control processor 320 adjusts the DAC 325 to an electrical signal representative of a predetermined light level as detected by the photodetectors and applies this level at the input of the first in the series of test channels of the integrator 342 and at the input of the reference integrator 340. The ratio of the actual output from the electrical measurement system 324 to the expected output is stored in memory and used as a gain calibration factor of the electrical measurement system 324.

Figure 7:
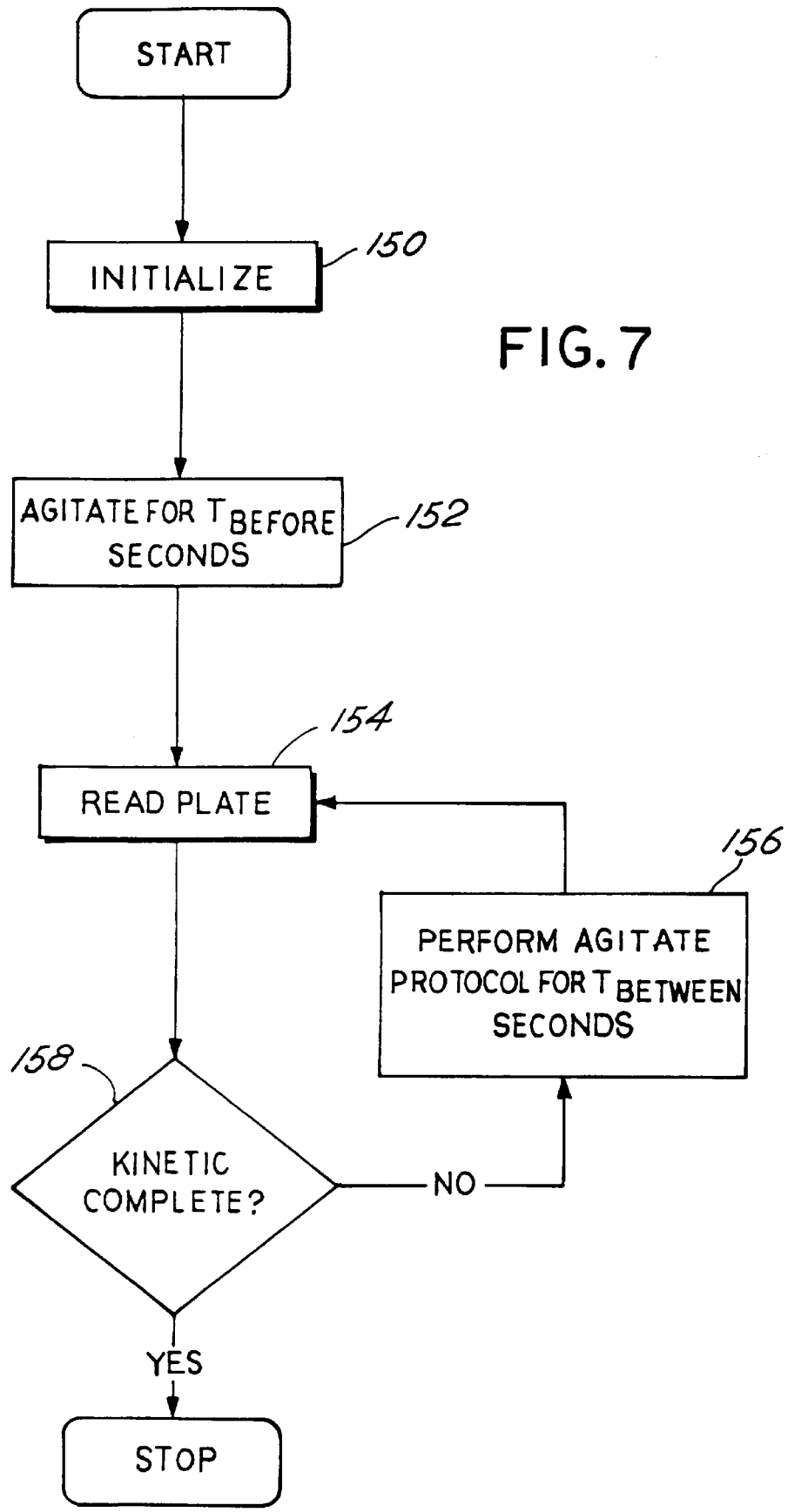
FIG. 7 is a flow chart of the general sequence of operation according to a preferred embodiment of the invention.

FIG. 7 is a flow chart illustrating the general sequence of operations according to the invention. The sequence begins with the initialization step 150 when the user uses the keypad 301 or the user interface computer 30 to establishing a measurement protocol and initiate a measurement. Step 150 configures the photometric device for end-point, spectrum, or kinetic measurements and determines the number and values of the wavelengths, spectrum parameters, agitation time intervals, dormant time intervals, vessels to be read; and other similar parameters.

Agitation of the multiplicity of samples contained in the multi-assay plate 12 may be selected by the user for a predetermined time prior to determining the optical properties of the samples. Sample agitation, in both step 152 and in step 156, is provided by the agitator means 20A, which includes a conventional stepper motor and belt-drive mechanism coupled to the multi-assay plate carrier means that supports and firmly holds the multi-assay plate and also linearly positions the columns of the vessels in the plate above photodetectors 88, as shown in FIG. 3a, in a sequential fashion. The agitator means imparts gentle oscillatory notion as a linear displacement parallel to top wall 101 and interior wall 109 of the multi-assay plate compartment 127, as shown in FIG. 3a. The amplitude of linear displacement comprising the oscillatory motion is about 1/16 of an inch at a sequence of alternating frequencies of about 20 Hz and about 30 Hz, each equal periods of approximately 125 milliseconds. This sequence of alternating agitation frequencies is continued for a time as short as 1 second up to any length of time selected by the user which may be as long as 1 minute, 1 hour, 1 day, or 1 week. Usually the agitation is continued for 3 seconds to provide for adequate mixing of liquid samples of from 50 to 400 microliters and having a viscosity about the same as water at 23*C. The agitation is followed by a predetermined delay time before the start of the read plate step 154. This delay time is selectable by the user within a time as short as about 200 milliseconds to as long as 1 minute, 1 hour, or 1 day.

Step 152 in FIG. 7 agitates the multi-assay plate 12 for the length of time as predetermined in the initialization step 150. Because some measurements, including some end point measurements, will not require the multi-assay plate 12 to be agitated, step 152 is not always applied.

Step 154 in FIG. 7 sequences through the predetermined wavelengths, optical distribution channels and the corresponding test channels in the integrator 342, and columns of the multi-assay plate 12 to read the transmission of light through each predetermined vessel and to calibrate each measurement for dark current offset and 100% transmission factor. The read plate step 154 is illustrated in greater detail in FIG. 8 below.

Multiple readings at multiple time intervals are typically desired for kinetic measurements, and these kinetic measurements are each accomplished by multiple passes through the flow chart illustrated in FIG. 7. End point and spectrum measurements are accomplished with a single pass. Following the read plate step 154, step 158 checks to determine if the system has completed all of the readings in a predetermined kinetic read cycle. If the answer in step 158 is no, step 156 optionally agitates the multi-assay plate 12 according to the protocol set in initialization step 150. In step 156 a kinetic reading typically includes a first time interval where the sample lies dormant, followed by an agitation time interval where the sample is vibrated, followed by a second time interval where the sample lies dormant. Each time interval is predetermined in initialization step 150. When step 156 completes, the sequence returns to step 154 for another reading in the kinetic cycle. Because some measurements do not require agitation between the readings, step 156 is not always applied. Steps 158, 156 and 154 are iterated by the system until the complete kinetic reading has been performed. If the answer in step 158 is yes, the sequence is complete.

Figure 8:
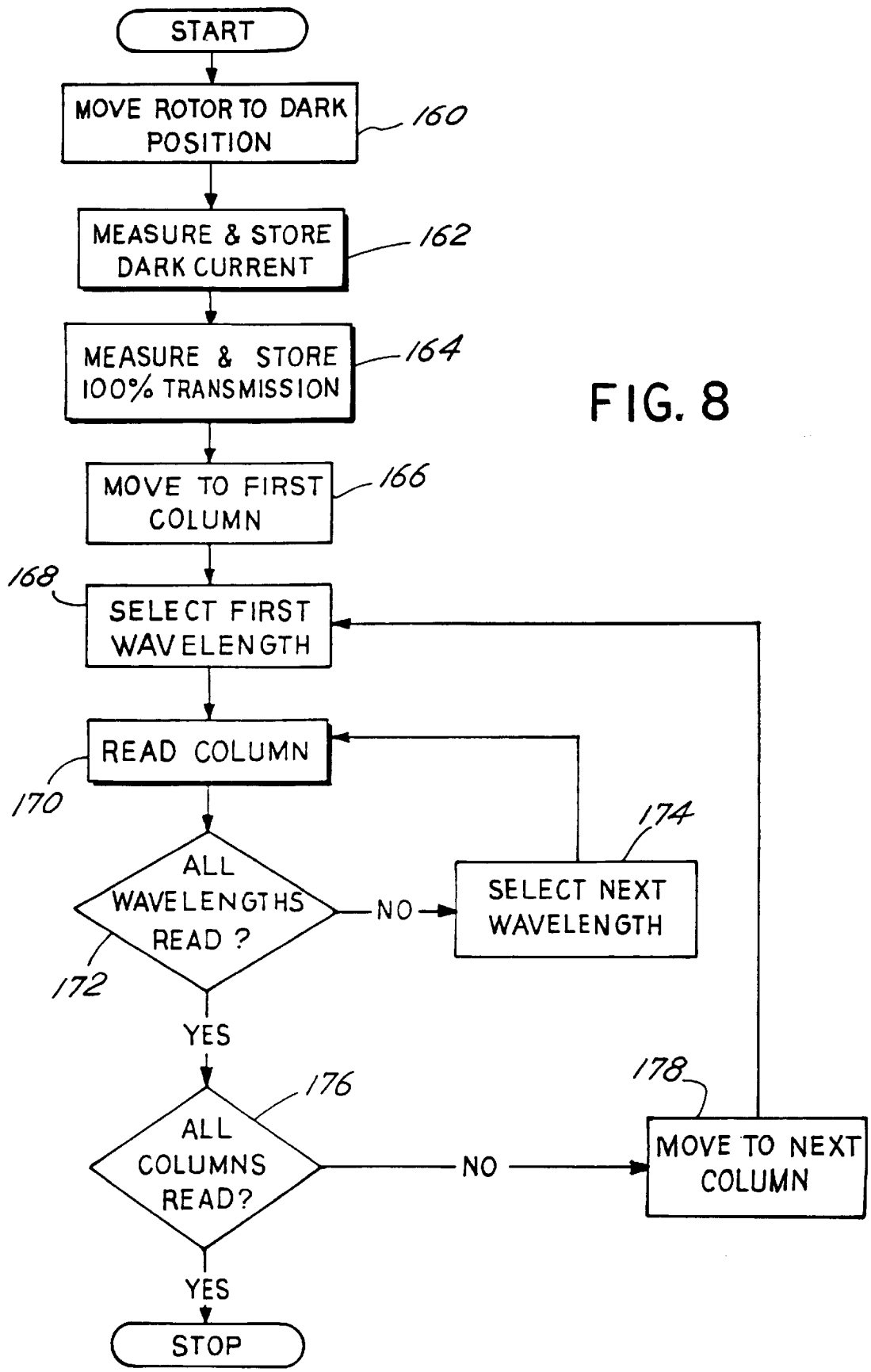
FIG. 8 is a flow chart of a measurement sequence for a preferred embodiment of the present invention utilizing a microplate.

FIG. 8 expands the read plate step 154 to illustrate the sequence of operations for reading the columns of the multi-assay plate 12 at selected wavelengths. Step 160 aligns the rotor 70 in a dark position where light is directed so that no light, illuminates the test photodetectors 88. Step 162 reads and stores in memory, a measurement offset known as "dark current" for each in the series of test channels in the integrator 342 for each gain setting and for the reference integrator 340. The respective dark currents are applied to the readings of the samples to correct for the effect of measurement offsets. The sequence to measure and store the dark currents is described in greater detail with reference to FIG. 9 below.

Step 164 in FIG. 8 reads and stores into memory the values for 100% transmission for each predetermined wavelength for each of the series of optical distribution channels and the corresponding test channels in the integrator 342. The respective 100% transmission values are applied to the readings of the test light transmitted through the samples in the multi-assay plate 12 to calculate the fraction of test light absorbed by the samples. The sequence to measure and store the 100% transmission values is described in greater detail in FIG. 10 below.

Step 166 moves the first column of vessels in the multi-assay plate 12 into position above the test photodetectors 88 for reading. A minimum delay interval of about 240 milliseconds is provided after the linear positioning and before test light is delivered to the first sample in a column so as to avoid substantially any effect of settling of fluid samples within the vessels. Step 168 selects the first predetermined wavelength. Step 170 reads each of the vessels in the column as illustrated in greater detail in FIG. 11. Step 172 checks to determine if all of the predetermined wavelengths have been read. If the answer is no, step 174 selects the next predetermined wavelength and returns the sequence to step 170. A wavelength selection means includes monochromator 54 which, in turn, includes a conventional stepper motor and diffraction grating drive mechanism to accurately position diffraction grating 59 to give 0.5 nanometer wavelength resolution for positioning light of a preselected wavelength range at monochromator exit alit 63, as shown in FIG. 2. The wavelength selection means provides for effecting step 174 within a time interval ranging from about 100 milliseconds for small wavelength steps of about 5 nanometers, to about 3 seconds for large wavelength steps of up to 500 nanometers (e.g., for positioning the monochromator from 250 to 750 nanometers). When all wavelengths are read the sequence goes forward to step 176 to determine if all of the preselected columns of the multi-assay plate 12 are read. If the answer is no, step 178 moves the next column of the multi-assay plate 12 into position and returns the sequence to step 168.

When the multi-assay plate 12 is moved from one column to the next, the settling of the samples may be effected and the resulting measurement of the optical properties of the samples in a kinetic measurements may be changed. The preferred embodiment illustrated in FIG. 8 sequences through the predetermined wavelengths before selecting the next column in order to minimize the number of times the multi-assay plate 12 is moved. An alternative embodiment sequences through the columns before selecting the next wavelength. This alternative sequence completes in less time than the preferred embodiment. The photometric device is capable of operating in either embodiment.

Figure 9:
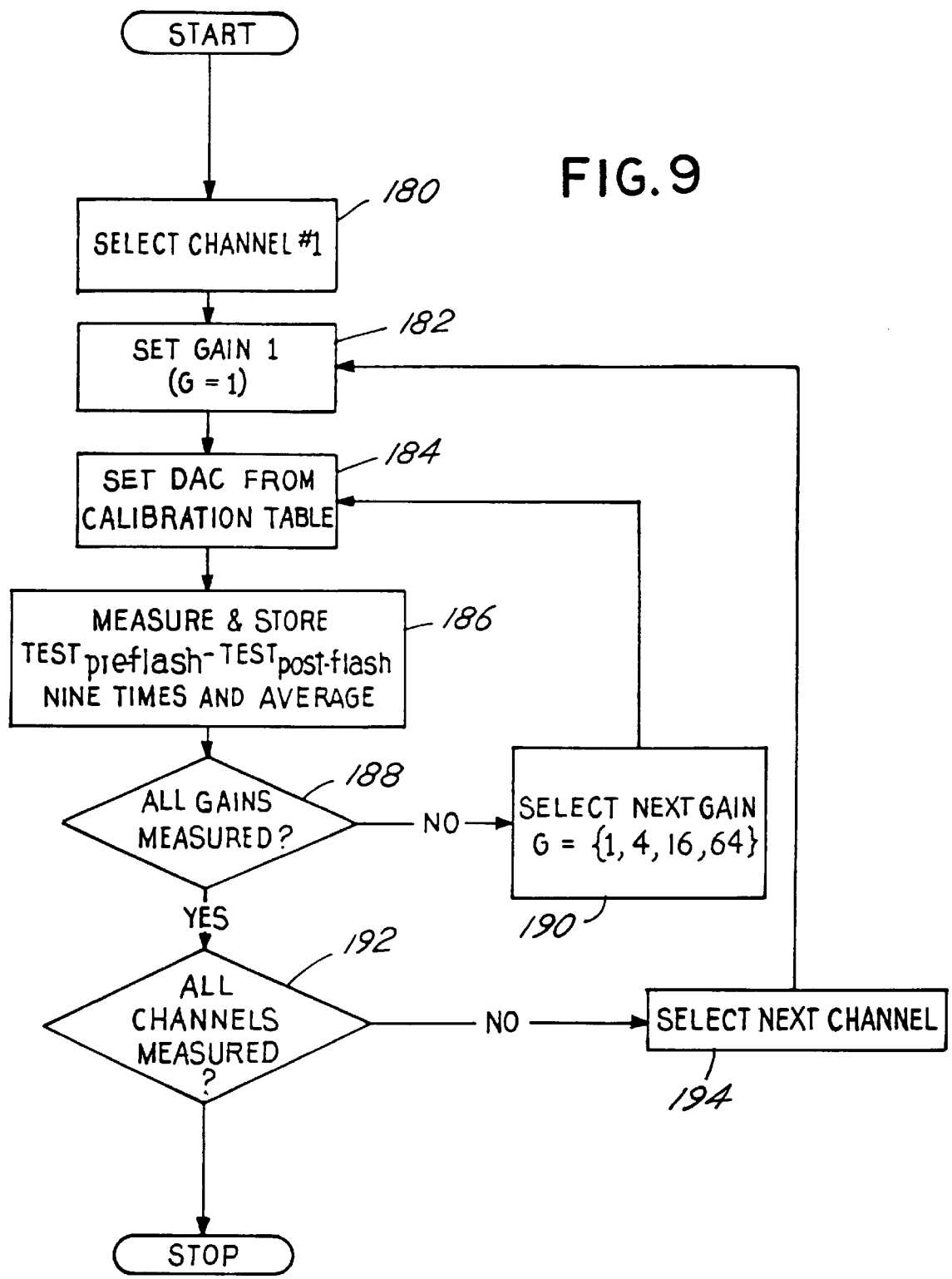
FIG. 9 is a flow chart of a dark current calibration sequence for the preferred embodiment of the present invention.

FIG. 9 expands step 162 to illustrate the sequence of operations that calibrate the photometric device for dark current. The dark current is the apparent light read by the electrical measurement system 324 when no light is transmitted. A primary source of dark current in the photometric device is an inherent voltage offset in the electrical measurement system 324. Each in the series of test channels in the integrator 342 is calibrated for each gain setting of the amplifier/ADC 323 and the reference integrator 340 is calibrated and respective calibration values are stored in memory. Coarse dark current offset calibrations were determined and stored as a part of the powerup sequence described in FIG. 6 above. The sequence in FIG. 9 determines residual dark current offset calibrations that remain after the coarse dark current offset calibration has been applied and stores these residual dark current offset calibrations in memory. The combination of the coarse and the residual dark current calibrations substantially eliminates dark current errors in the measurement of samples.

The sequence in FIG. 9 starts at step 180 which selects a first channel of the integrator 342. Step 182 selects a gain of one (1) in the amplifier/ADC 323. At step 184 the DAC 325 applies the coarse dark current offset calibration, determined and stored in memory during the powerup sequence described in FIG. 6, to the input of the selected channel of the integrator 342. This coarse dark current offset calibration is approximately equal and of opposite sign to the inherent voltage offset in the electrical measurement system 324.

Step 186 aligns the rotor 70 to a dark position where light does not pass to the series of distribution optical fibers 76 or to the test photodetectors 88. Step 186 reads the apparent test light for the selected channel of the integrator 342 by subtracting the test "post-flash" reading from the test "pre-flash" reading as described in greater detail in the electrical timing diagram in FIG. 5 above. Step 186 takes nine readings, computes the average, and stores this average in memory as residual dark current offset calibration. The light excitation source 50 is flashed in each calibration reading so that a voltage offset in the electrical measurement system 324 due to radiated or conducted coupling into the electrical measurement system 324 will appear in the calibration sequence in the same manner as in a reading of a test sample in a measurement sequence.

The test dark current is calibrated for each of the amplifier/ADC 323 gains one (1), four (4), sixteen, (16), and sixty four (64). Step 188 checks to determine if all gains have been calibrated. If the answer is no, step 190 selects the next gain in the order and returns to step 184. If the answer in step 188 is yes, step 192 checks to determine if all the test channels in the integrator 342 have been measured. If the answer is no, step 194 selects the next channel in the integrator 342 and returns the sequence to step 182. If the answer in step 192 is positive, the sequence is complete and all of the channel of the integrator 342 and all of the gains of the amplifier/ADC 323 have been calibrated for dark current.

Reference dark current is calibrated using a similar sequence. The filter wheel 56 is moved to a dark position where light does not pass to the monochromator 54 or to the reference photodetector 64. Reference dark current is measured by subtracting the reference "pre-flash" reading from the reference "post-flash" reading as described in greater detail in the electrical timing diagram in FIG. 5 above.

Figure 10:
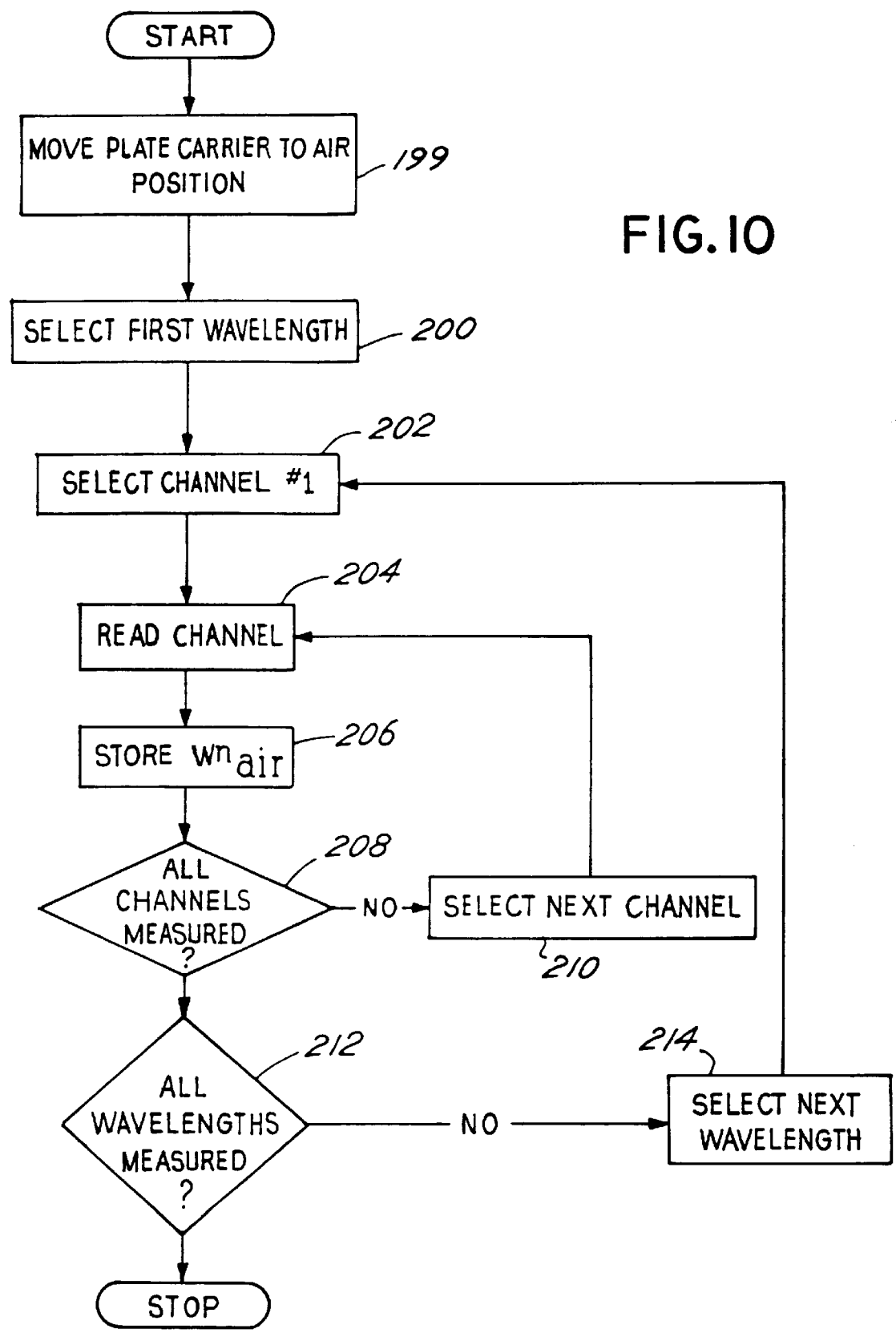
FIG. 10 is a flow chart of a transmission calibration sequence.

FIG. 10 expands step 164 to illustrate the sequence of operations in which 100% transmission values are measured and stored for each predetermined wavelength for each of the series of optical distribution channels and the corresponding test channels in the integrator 342. Starting FIG. 10 at step 199 the sequence moves the plate carrier 20 where the test light illuminates the test photodetectors 88 directly through air without passing through the multi-assay plate 12. Step 200 selects the first predetermined wavelength. Step 202 aligns the rotor 70 to illuminate the first in the series of distribution optical fibers and selects the first channel of the integrator 342. Alignment of rotor 70 from a first distribution optical fiber in the series to the second distribution optical fiber in the series requires about 30 milliseconds, which incorporates both a moving phase and a settling phase. Step 204 reads an absorption for air as shown in the measurement of $W^n$ described in greater detail in FIG. 12 below. Step 206 stores the $W^n$ measured above as $W^{nair}$. Step 208 checks to determine that 100% transmission values have been obtained for each in the series of optical distribution channels and the corresponding test channels in the integrator 342. If the answer is no, step 210 aligns the rotor to the next in the series of distribution optical fibers, selects the next in the series of test channels in the integrator 342, and returns the sequence to step 204. If the answer to step 208 is yes, step 212 checks to determine if all the predetermined wavelengths have been read. If the answer is no, step 214 selects the next wavelength in the sequence and returns to step 202. If the answer to step 214 is yes, the sequence is complete.

Figure 11:
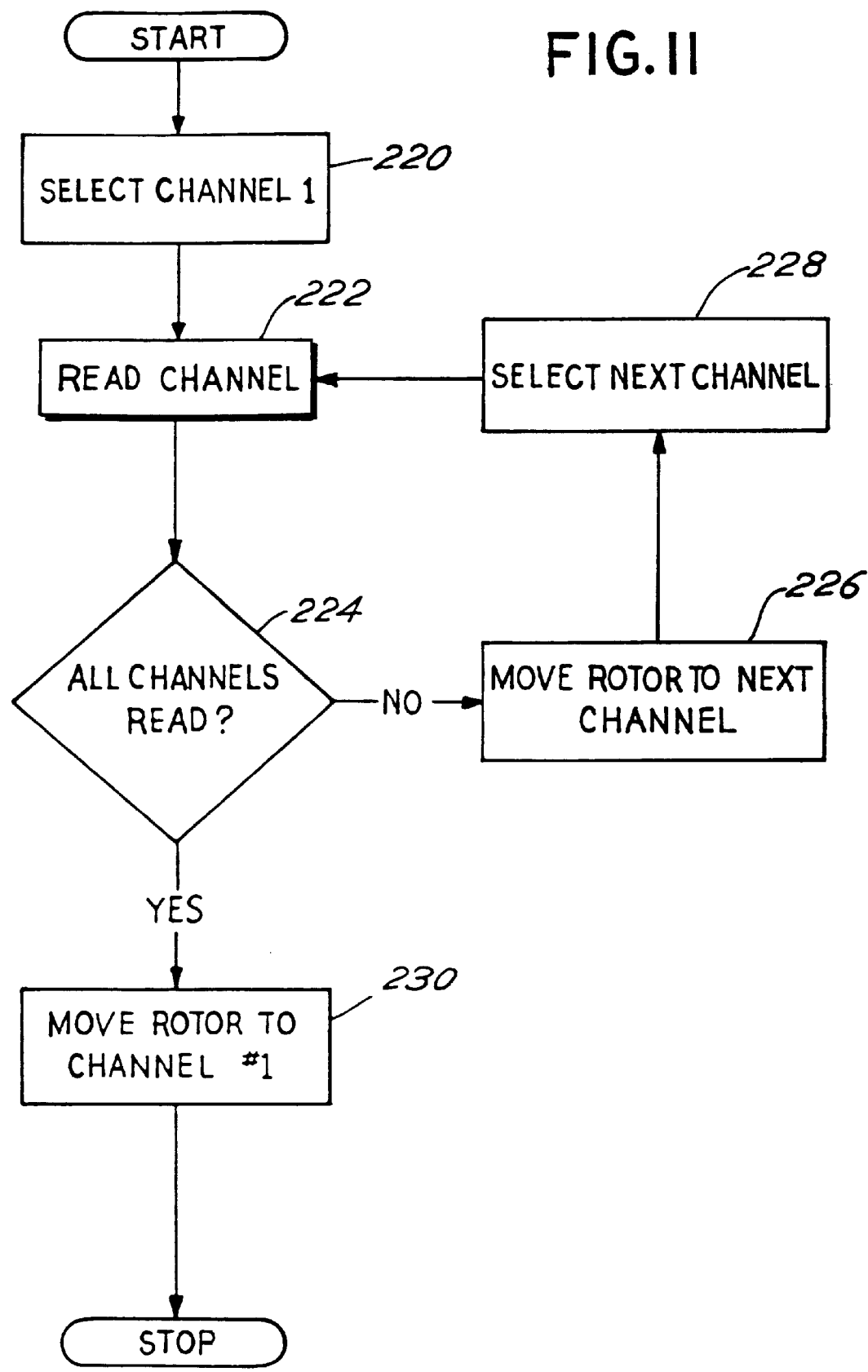
FIG. 11 is a flow chart of an operational measurement sequence with respect to a column of a multi-assay plate according to a preferred embodiment of the present invention.

FIG. 11 expands step 170 to illustrate the sequence of operations involved in reading a column of vessels in the multi-assay plate 12. Beginning at step 220 the CPU 320 directs the rotor 70 to align the test light to the first in the series of distribution optical fibers 76 and the acquisition and control processor 320 selects the first in the series of test channels in the integrator 342. Step 222 reads the test light transmitted through a sample in a selected vessel as described in greater detail in FIG. 12 below. Step 224 checks to determine if all of the channels have been read. If the answer is no, step 226 aligns the rotor 70 to the next in the series of distribution optical fibers 76. Step 228 selects the next channel in the integrator 342 and returns the sequence to step 222. If the answer to step 224 is yes, step 230 aligns the rotor 70 to the first in the series of distribution optical fibers 76 to complete the sequence.

Figure 12:
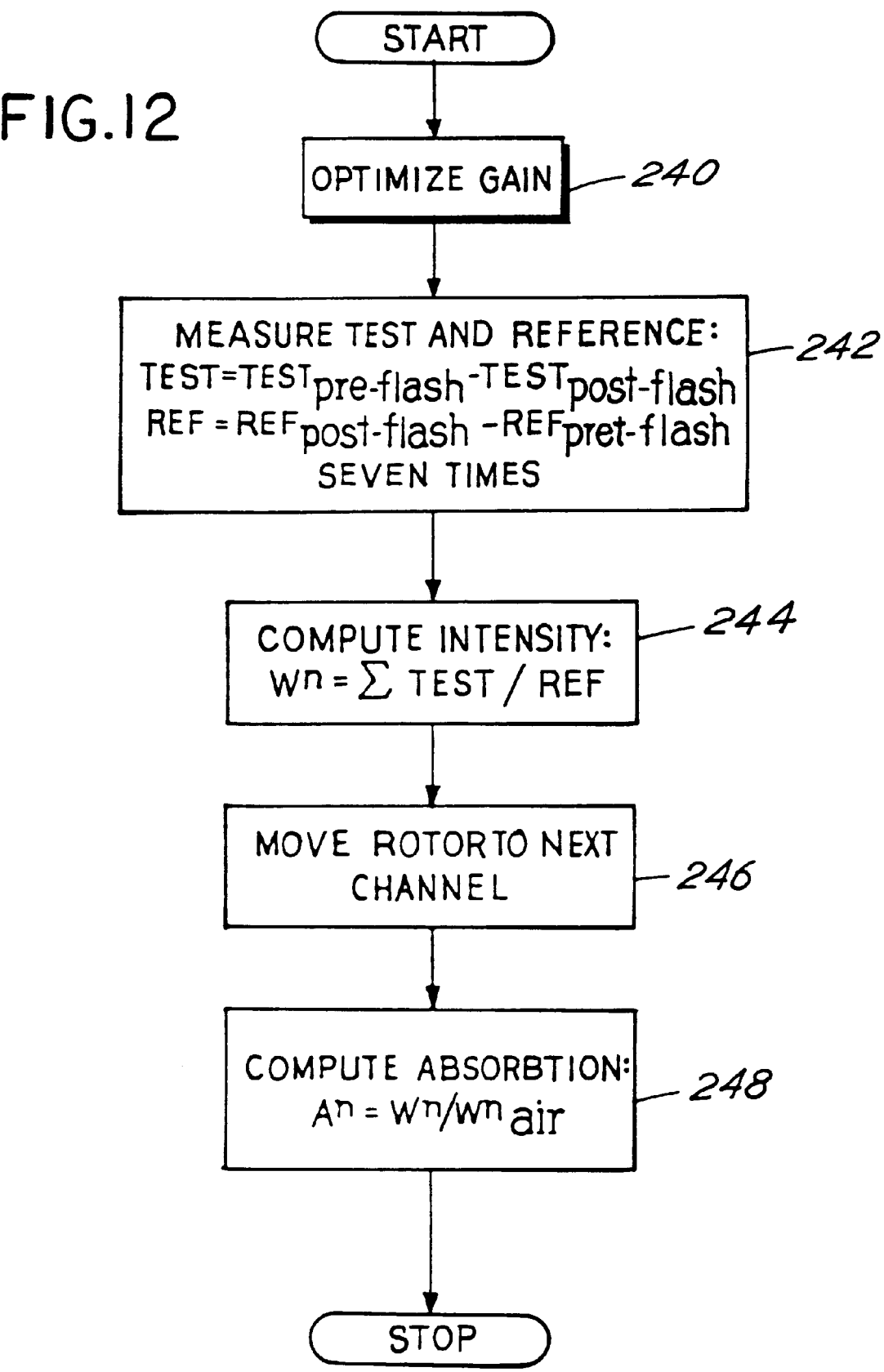
FIG. 12 is a flow chart of a sample measurement sequence.

FIG. 12 expands step 204 and step 222 to illustrate the sequence of operations involved in measuring the optical properties of a sample. The sequence starts with step 240, illustrated in greater detail in FIG. 13 below, to optimize the gain of the electrical measurement system 324. Step 242 measures the test light detected by the test photodetectors 88 and the reference light detected by the reference photodetector 64. The excitation light source 50 emits a series of light flashes. Step 242 measures test light transmitted to the test photodetectors 88, by subtracting the test "post-flash" reading from the test "pre-flash" reading and measures reference light transmitted to the reference photodetector 64, by subtracting the reference "pre-flash" reading from the reference "post-flash" reading. The measurement process is described in greater detail in the electrical timing diagram in FIG. 5 above. Step 242 is repeated 7 times and the results summed. Step 244 computes $W^n$, an uncalibrated reading of absorption of a sample under test, by dividing the test light measured in step 242 by the reference light measured in step 242. Step 246 aligns the rotor 70 to the next optical distribution channel. Step 248 completes the sequence by computing $A^n$, a calibrated reading of absorption of a sample under test, by multiplying the uncalibrated reading, $W^n$, by the inverse of the corresponding 100% transmission value $W^{nair}$, measured and stored in step 206.

Figure 13:
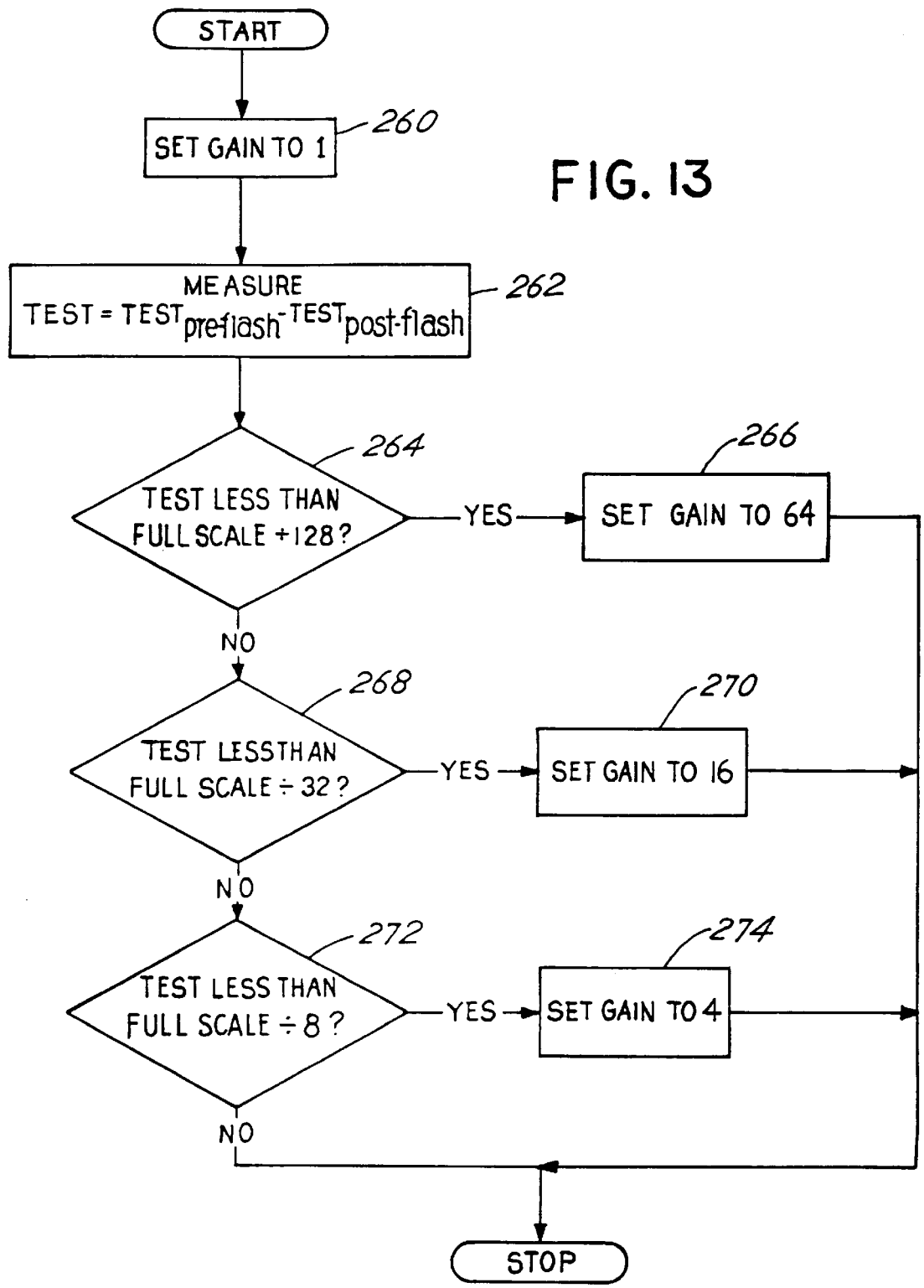
FIG. 13 is a flow chart of an optimization sequence for the electrical components of a preferred embodiment of the present invention.

FIG. 13 expands step 240 to illustrate the sequence of operations involved in optimizing the gain of the electrical measurement system 324. Four gain settings are used in the amplifier/ADC 323 to give the photometric device a measurement range of five orders of magnitude when measuring the absorption of a sample. If the gain is set too high, saturation of the circuits in the electrical measurement system 324 will cause the photometric device to display an erroneous reading. If the gain is set too low, electrical noise will degrade the precision and sensitivity of the reading.

Starting at step 260, the gain of the amplifier/ADC 323 is set to one (1). Step 262 measures the test light transmitted to the test photodetector 88 by subtracting the test "post-flash" reading from the test "pre-flash" reading as described in greater detail in the electrical timing diagram in FIG. 5 above. Step 264 checks to determine if this level divided by one hundred twenty eight (128) is less than the full scale of the amplifier/ADC 323. If the answer is yes, step 266 sets the amplifier/ADC 323 channel gain to sixty four (64), the sequence is complete and the gain has been optimized. If the answer is no, step 268 checks to determine if the level measured in step 262 divided by thirty two (32) is less than the full scale of the amplifier/ADC 323. If the answer is yes, step 270 sets the amplifier/ADC 323 gain to sixteen (16), the sequence is complete and the gain has been optimized. If the answer is no, step 272 checks to determine if the level measured in step 262 divided by eight (8) is less than the full scale of the amplifier/ADC 323. If the answer is yes, step 274 sets the amplifier/ADC 323 gain to four (4), the sequence is complete and the gain has been optimized. If the answer is no, the gain is left at one (1) and the sequence is complete.

Figure 14:
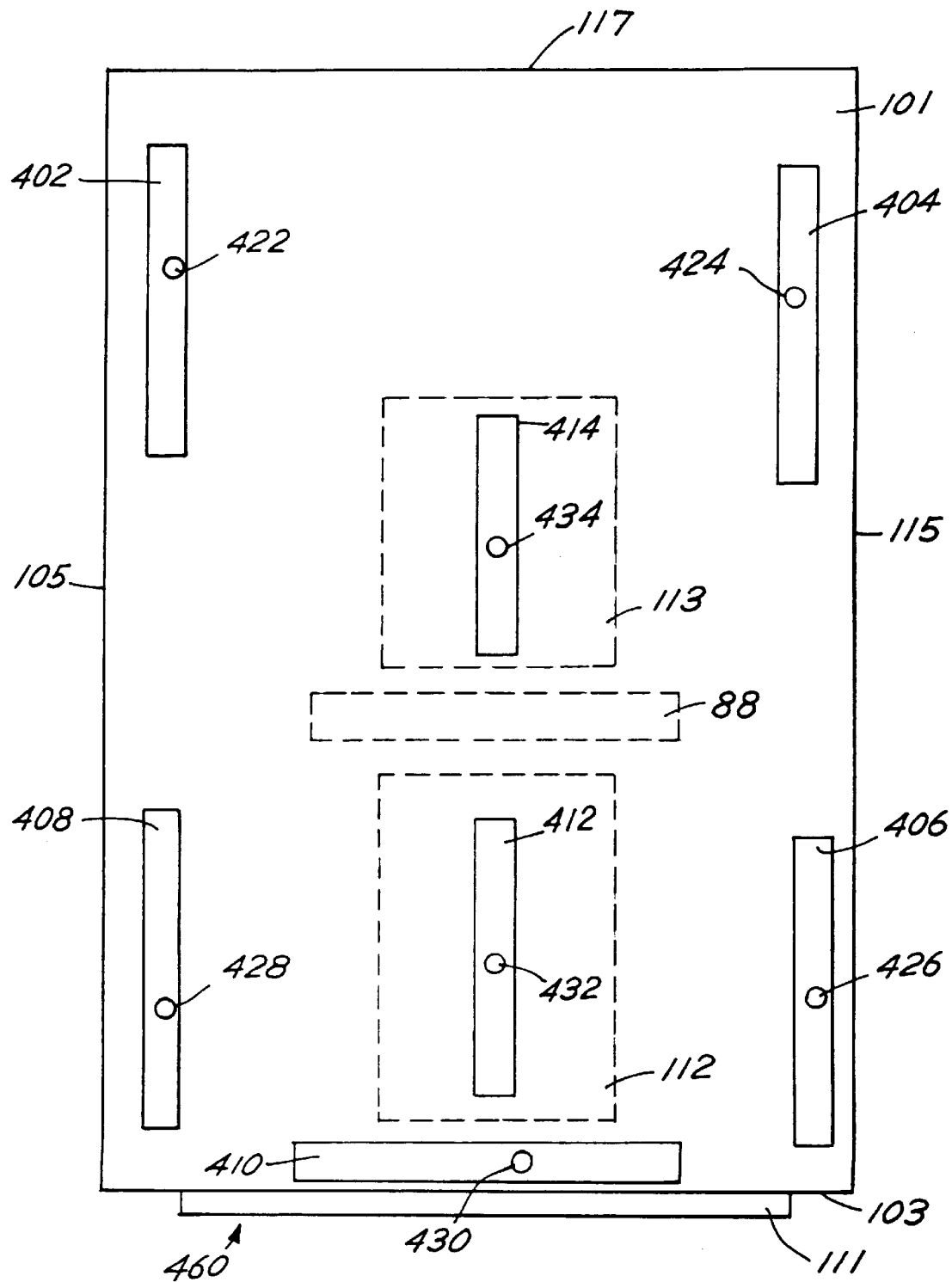
FIG. 14 is a schematic top view of the chamber of the photometric device showing a second heating system embodiment.
Figure 15:
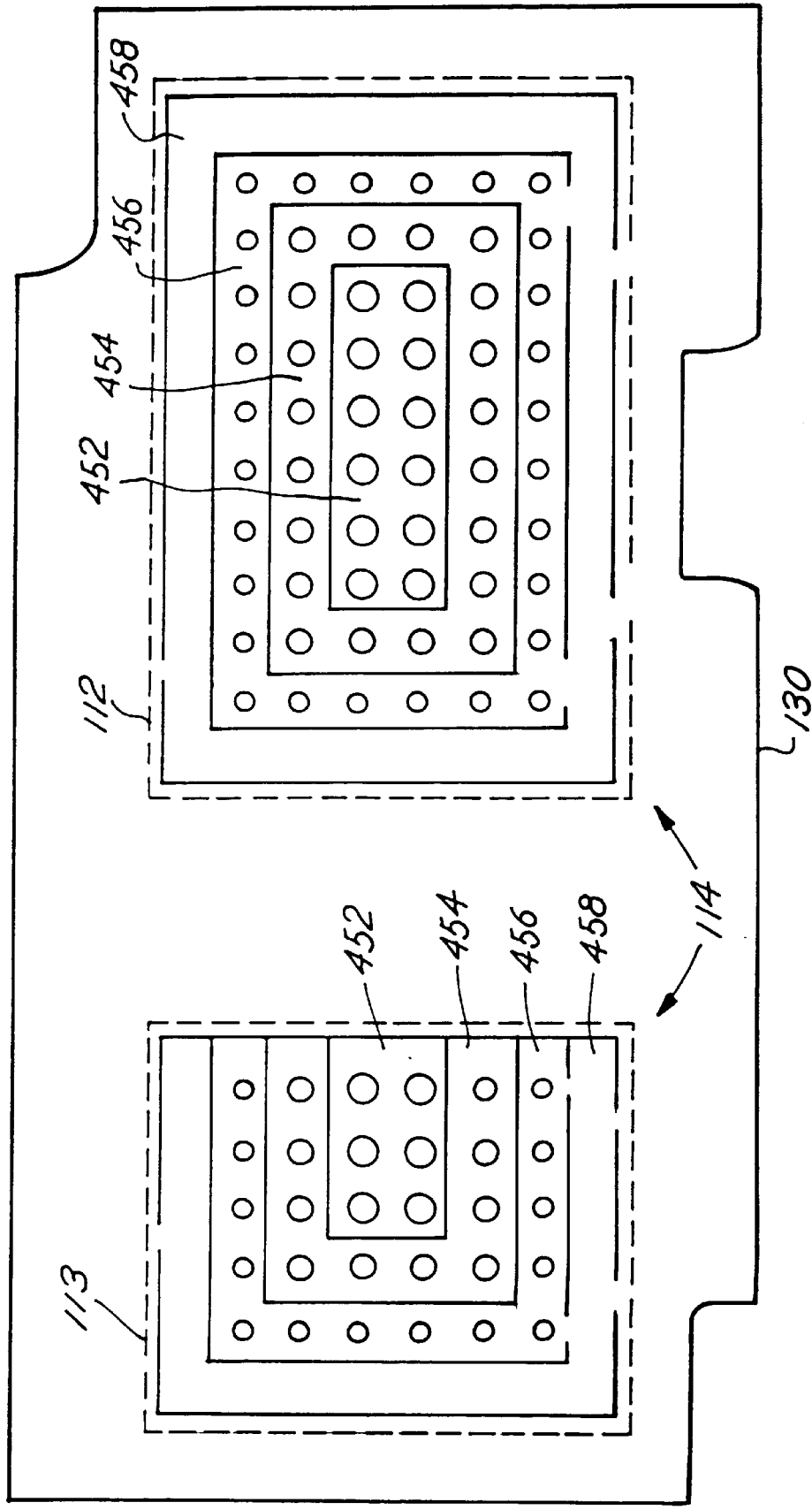
FIG. 15 is a top view of the baffle incorporated into the heating system embodiment shown in FIG. 14.

Referring now to FIGS. 14 and 15, another preferred embodiment of the temperature control means 28 is shown. This embodiment provides enhanced temperature control in the form of a more uniform rate of heating from the initial entry temperature to the preselected measurement temperature and better maintenance of the preselected temperature once achieved.

A multiplicity of wall heating elements and associated temperature sensors are placed in different regions of the walls of multi-assay plate compartment 127 so as to create separate radiative heating zones in the compartment. As in the previous embodiment, substantially all of the walls enclosing the multi-assay plate compartment 127 have a temperature greater than the temperature of the air or other convection gas passing through the apertures 114. In this way, condensation, within the photometric device 10 or on any cover (not shown) that may be placed over multi-assay plate 12, is substantially prevented. The multiplicity of heating elements and temperature-sensing elements may be disposed on any of the walls enclosing the multi-assay plate compartment 127, including top wall 101, interior wall 109, front side wall 105, back side wall 115, door-side wall 103, or door-opposed side wall 117, or any other surface in thermal communication with one or more of these walls.

As shown in FIG. 14, this preferred embodiment includes seven (7) heating elements and seven (7) temperature-sensing elements placed, in pairs, at preselected locations on top wall 101. A peripheral wall heating element 402 and peripheral wall temperature-sensing element 422 are located near the vertex of walls 101, 105 and 117. A peripheral wall heating element 404 and peripheral wall temperature-sensing element 424 are located near the vertex of walls 101, 115 and 117. A peripheral wall heating element 406 and peripheral wall temperature-sensing element 426 are located near the vertex of walls 101, 115 and 103. A peripheral wall heating element 408 and peripheral wall temperature-sensing element 428 are located near the vertex of walls 101, 103 and 105. Minor central heating element 414 and minor central temperature-sensing element 434 are located immediately above the minor post-heating plenum 113. Major central heating element 412 and major central temperature-sensing element 432 are located immediately above the major post-heating plenum 112. Finally, a door heating element 410 and a door temperature-sensing element 430 are located near side wall 103 and in the vicinity of door 111. FIG. 14 also shows the placement of the respective heater and sensor elements with respect to the test photodetectors 88.

The heating elements are embedded in the walls or door. The inner wall portion is aluminum or other suitable heat-conducting material such as brass, steel, copper, or the like, and the outer wall portion is the insulation 134, as described previously. The temperature-sensing elements are placed on the surface of the walls facing multi-assay plate 12. Direct radiative imaging of the heating elements onto the samples is thereby substantially avoided, and the sensors sense the same wall temperature as seen radiatively by the samples.

The heating elements substantially reduce ambient temperature effects and add supplemental radiative heating uniformly throughout the compartment 127. The temperature sensors 422, 424, 426, 428, 430, 432 and 434 are connected to the appropriate separate channels of temperature-sensing circuit 326 shown in FIG. 4. In this embodiment, temperature-sensing circuit 326 has at least nine (9) separate temperature-sensing channels. The multiplexed outputs of circuit 326 are led to amplifier/ADC 323, which is in electrical communication with control processor 320 which, in turn, is in electrical communication with heating element control circuit 328. In this embodiment, heating element control circuit 328 also has at least nine (9) separate output channels. A separate output channel is connected to each of heating elements 402, 404, 406, 408, 412 and 414 in an appropriate fashion so that heater 402 and sensor 422; heater 404 and sensor 424; heater 406 and sensor 426; heater 408 and sensor 423; heater 410 and sensor 430; heater 423 and sensor 432; as well as heater 414 and sensor 434 work together as pairs in seven (7) separate control loops. These seven separate control loops work in a similar fashion to the two (2) separate control loop pairs formed by wall heater 126 and sensor 128, and by air heater 108 and air temperature sensor 110, as disclosed above and as shown in FIG. 4. The nine (9) separate temperature control loops are controlled by standard temperature circuitry as is well-known in the art of temperature control. The multiplicity of heating elements form a multiplicity of radiative heating zones within multi-assay plate compartment 127 and provide for maintaining a uniform steady-state temperature in each of the samples contained in a multiplicity of vessels on the multi-assay plate.

In yet another preferred embodiment, each of heating elements 402, 404, 406, 408, 412, 414, and 126 may be controlled in a single control loop. In this case the relative power consumption of the respective heating elements 402, 404, 406, 408, 412, 414, and 126 in the previous embodiment is first measured for a given configuration and construction of chamber means 16 with a given placement of the heating elements 402, 404, 406, 408, 412, 414 and 126 into their respective radiative heating zones. This measurement is averaged over the time required to heat the samples of a multi-assay plate from room temperature to 37° C., the latter which is a frequently utilized final temperature for biochemical measurements. The relationship of heating power consumed by the heating elements, one with respect to the other, is adopted as a final fixed specification for the relationship between each of the heating elements. In this embodiment, a single temperature sensor 428 is connected to an appropriate channel of temperature-sensing circuit 326 shown in FIG. 4 to initiate a control loop. Also in this embodiment, temperature-sensing circuit 326 minimally requires only two (2) separate temperature-sensing channels, one for control of air-heating element 108 and one for control of heating elements 402, 404, 406, 408, 412, 414 and 126. The multiplexed outputs of circuit 326 are led to amplifier/ADC 323, which is in electrical communication with control processor 320 which, in turn, is in electrical communication with heating element control circuit 328. In this embodiment, heating element control circuit 328 need only have two (2) separate output channels. The appropriate output channel is connected to the air-heating element 108 and the other to heating elements 402, 404, 406, 408, 412, 414 and 126 which may be operated either in parallel or in series. As for the previous embodiment, the multiplicity of heating elements form a multiplicity of radiative heating zones within multi-assay plate compartment 127 and provide for maintaining a uniform steady-state temperature in each of the samples contained in a multiplicity of vessels on the multi-assay plate.

In the preferred embodiment, the apertures 114 in baffle 130 are adjusted to concentrate the flow of heated convection air, or other heated inert convection gas such as nitrogen, argon, helium, carbon dioxide, or the like, to preselected regions of the lower surface of the multi-assay plate 12. The preselected convection flow rates to preselected regions of the multi-assay plate further facilitate a rapid uniform heating rate and subsequent temperature maintenance. An aperture 114 is placed in direct opposition to each inner vessel of the multi-assay plate 12 when it is positioned above major post-heating plenum 112, as best shown in FIGS. 3a and 15. Thus for 96-well multi-assay plates, having sixty (60) inner vessels, i.e., vessels which are not on the periphery, there are 60 apertures 114 in the portion of baffle 130 situated above major post-heating plenum 112. These apertures are arranged in the same geometric pattern and spacing as the vessels within the 96-well multi-assay plate. For example, in a 96-vessel multi-assay plate having an 8×12 pattern with 9 mm center-to-center spacing, apertures 114 are arranged in an 6×10 pattern with 9 mm center-to-center spacing.

The size of the apertures 114 also varies. The inner 12 apertures 452 have about a 3 millimeter diameter; the penultimate innermost 20 apertures, immediately surrounding the inner 12 apertures, have a diameter of about 2 millimeters. The next outermost 28 apertures have a diameter of about 1 millimeter. The outermost 36 vessels of the 96-well multi-assay plate are not directly opposed by any aperture 114 but heat quickly due to the inherently enhanced peripheral surface area, as discussed previously.

Apertures 114 also are provided in the portion of baffle 130 situated above the minor post-heating plenum 113, as shown in FIG. 15, in order to uniformly heat and maintain the measurement temperature of the samples within this region. There are 30 such apertures situated above the minor post-heating plenum 113. The diameter and placement of these apertures, one with respect to the other, is identical to that of the 30 apertures situated above the major post-heating plenum 112 nearest to the test photodetectors 88, as shown in FIG. 15.

Together, the radiative heating elements, located to provide coordinated radiative heating zones, and the modified heat distributing baffle, concentrating heated air to the central portion of the multi-assay plate, cooperate to define radiative/convection heating means, generally designated 460 in FIG. 14, for substantially offsetting ambient effects, reducing air circulation above the samples and preserving substantially uniform heat distribution within the multi-assay plate 12. The samples contained therein are thus more rapidly and uniformly heated to the preselected temperature and temperature maintenance is substantially enhanced.

The above-described embodiments of the present invention will perform a single measurement optical property analysis of a microplate, 8×12 vessels, in about 9 seconds. In a multi-assay plate with less than twelve columns, the time is reduced proportionately. With sequential repetition of such measurements to determine the kinetically-changing optical properties of the samples, the interval between such repetitive measurements is about 9 seconds, a speed presently unattainable in a photometric device of this scope and extent. Optionally, the sequential repetition of such measurements may include agitation step 156, which may be as short as about 1 second thereby increasing the time interval selectably to 10 seconds. The optical properties may be made at any wavelength of light, selectable by the user in intervals of 1 nanometer steps, between 250 and 750 nanometers so that a spectrum of optical properties of the multiplicity of samples may be monitored in a kinetic fashion, which optionally may include agitation step 156. Optical properties measured by photometric devices incorporating the disclosed invention include light absorbance, light scattering, fluorescence and/or phosphorescence.

While preferred embodiments of the present invention have been shown and described, it will be apparent to those skilled in the art that various changes and modifications may be made without departing from the true scope and spirit of the present invention. For that reason, the present invention is defined by the following claims.

What is claimed is:

1. A photometric device for measuring an optical parameter of a plurality of samples, contained within a plurality of sample sites disposed on a multi-site assay plate, comprising:

an excitation light source comprising a flash lamp that emits a light having a first wavelength range on the order of 200 to 1,000 nanometers for providing test light to eight or more of said sample sites;

a light distribution network, including a series of distribution optical fibers, for transmitting said test light substantially vertically through two or more of said sample sites;

a plurality of photodetectors for receiving emitted light from said eight or more sample sites and providing electrical signals relating to the intensity of said test light as passed by said two or more samples;

vibrating means for imparting repeated oscillatory movement of said multi-site assay plate for a predetermined time before each of a series of at least two measurement of said optical parameter at said two or more sample sites;

means for kinetic analyzing said electrical signals;

monochromator means for receiving excitation light from said excitation light source and for transmitting a preselected wavelength bandpass fraction thereof defining a means wavelength between 250 and 750 nanometers, to said light distribution network; said monochromator means including a diffraction grating and further including a light-emission slit, said light distribution network including a plurality of optical fibers coupled to said light-emission slit; and coupling means for coupling said monochromator means to said light distribution network such that said mean wavelength of said test light delivered to each of said eight or more sample sites varies by less than one nanometer.

2. The photometric device according to claim 1 further comprising a series of reference photodetectors, each of said optical fibers being associated with one of said reference photodetectors, respectively.

3. The photometric device according to claim 1 further comprising a multi-assay plate compartment for substantially enclosing said multi-assay plate and for maintaining said samples at a substantially uniform predetermined temperature during measurement of said optical parameter.

4. The photometric device according to claim 3 further comprising temperature control means for providing a stream of heated air to said multi-assay plate.

5. The photometric device according to claim 4, further comprising a temperature control means for providing a stream of heated air to said multi-assay plate, said temperature control means including:

air-heating means for providing said heated air;

air-compression means for compressing said heated air;

a plenum for storage of said heated compressed air; and a baffle, interposed said plenum and said multi-assay plate, having apertures distributing said heated compressed air in a predetermined pattern upon said multi-assay plate.

6. The photometric device according to claim 5 wherein said flash lamp is a xenon flash lamp.

7. A photometric device for measuring an optical property of a plurality of samples, contained within a plurality of vessels in a multi-assay plate, comprising, in combination;

an excitation light source comprising a flash lamp that emits light flashes having a wavelength range on the order of 200 to 1100 nanometers;

a monochromator, responsive to said light flashes received from said excitation light source, for producing a substantially monochromatic test light that is continuously selectable within a range of about 250 to 750 nanometers having a predetermined bandpass width of about 1–20 nanometers;

a distribution network transmitting said substantially monochromatic test light substantially vertically through said vessels, said substantially monochromatic test light being affected by each of said samples; and photodetector means for receiving said substantially monochromatic test light affected by each of said samples and responsively providing a plurality of electrical measurement output signals representative of said optical property for each of said samples, respectively.

8. A photometric device as claimed in claim 7 further comprising:

temperature control means, substantially enclosing said multi-assay plate in a closed state, for regulating the temperature of said samples during measurement, said temperature control means including supply means for generating a stream of heated air and a baffle, interposed said multi-assay plate and said supply means, said baffle having central apertures and peripheral apertures directing said heated air against said multi-assay plate and about said vessels; and microprocessor means, coupled to said excitation light source, to said photodetector means and to said temperature control means, for controllably activating said flash lamp, analyzing said output signals in accordance with said light flashes, respectively, and controllably activating said supply means.

9. A photometric device as claimed in claim 7 wherein the wavelength range for the light flashes is a continuum and said monochromator includes a diffraction grating and slit means for providing the continuously selectable wavelength range.

10. The photometric device according to claim 7 wherein said monochromator includes a diffraction grating.

11. The photometric device according to claim 4 wherein said monochromator further comprises a light-emission slit, said optical distribution network including a plurality of optical fibers coupled to said light-emission slit.

12. A photometric device as claimed in claim 7 further comprising an optical fiber, coupled to said monochromator for receiving said substantially monochromatic test light and transmitting said substantially monochromatic test light to said samples.

13. A photometric device as claimed in claim 12 wherein said optical fiber includes a series of distribution optical fibers that serve as said optical distribution network.

14. A photometric device as claimed in claim 12 further comprising beam splitter means for diverting a portion of said substantially monochromatic test light to provide a corresponding reference light and for delivering said reference light to reference photodetector means.

15. A photometric device as claimed in claim 14 wherein said beam splitter means interposes said optical fiber and said vessels.

* * * * *